US007728105B2

(12) United States Patent  
Morgan et al.

(10) Patent No.: US 7,728,105 B2
(45) Date of Patent: Jun. 1, 2010

(54) PEPTIDES IMPAIRING PBX DEPENDENT GENE REGULATION

(75) Inventors: Richard George Leonard Morgan, London (GB); Ruth Pettengell, London (GB); Nicolas Pierre Benoît Forraz, Surrey (GB); Colin Patrick McGuckin, Surrey (GB)

(73) Assignee: St. George's Hospital Medical School, London (GB)

( * ) Notice: Subject to any disclaimer, the term of this patent is extended or adjusted under 35 U.S.C. 154(b) by 331 days.

(21) Appl. No.: 10/538,723

(22) PCT Filed: Dec. 12, 2003

(86) PCT No.: PCT/GB03/05425

§ 371 (c)(1),
(2), (4) Date: Mar. 24, 2006

(87) PCT Pub. No.: WO2004/055049

PCT Pub. Date: Jul. 1, 2004

(65) Prior Publication Data

US 2006/0234938 A1 Oct. 19, 2006

(30) Foreign Application Priority Data

Dec. 13, 2002 (GB) ................... 0229151.6

(51) Int. Cl.
*C07K 14/00* (2006.01)
(52) U.S. Cl. .............................. 530/324; 514/2; 530/328; 530/325
(58) Field of Classification Search ................. 514/2; 530/326, 327, 328, 329, 324, 325
See application file for complete search history.

(56) References Cited

U.S. PATENT DOCUMENTS

| 6,551,795 | B1 * | 4/2003 | Rubenfield et al. ......... 435/69.1 |
| 2002/0086383 | A1 | 7/2002 | Sauvageau et al. |
| 2003/0124128 | A1 * | 7/2003 | Lillie et al. ............. 424/155.1 |
| 2004/0053233 | A1 * | 3/2004 | Lorens et al. ................ 435/6 |

FOREIGN PATENT DOCUMENTS

| WO | WO-97/42222 A1 | 11/1997 |
| WO | WO-2004/033672 A2 | 4/2004 |
| WO | WO-2004/055049 A1 | 7/2004 |

OTHER PUBLICATIONS

Antonchuk et al., "*HOXB4*—Induced Expansion of Adult Hematopoietic Stem Cells Ex Vivo," *Cell*, 109: 1-20, 2002.
Ayton et al., "Transformation of myeloid progenitors by MLL oncoproteins is dependent on *Hoxa 7* and *Hoxa 9*," *Genes & Development*, 17: 2298-2307, 2003.
Chang et al., "Pbx Modulation of Hox Homeodomain Amino-Terminal Arms Establishes Different DNA-Binding Specificities across the *Hox* Locus," *Molecular and Cellular Biology*, 16(4): 1734-1745, 1996.
Piper et al., "Structure of a HoxB1-Pbx1 Heterodimer Bound to DNA: Role of the Hexapeptide and a Fourth Homeodomain Helix in Complex Formation," *Cell*, 96: 587-597, 1999.
Kyba et al., "HoxB4 Confers Definitive Lymphoid-Myeloid Engraftment Potential on Embryonic Stem Cell and Yolk Sac Hematopoietic Progenitors," *Cell*, 109: 29-37, 2002.
Mann et al., "Extra specificity from *extradenticle*: the partnership between HOX and PBX/EXD homeodomain proteins," *TIG*, 12(7): 258-262, 1996.
Passner et al., "Structure of a DNA-bound Ultrabithorax-Extradenticle homeodomain complex," *Nature*, 397: 714-719, 1999.
Antonchuk et al., "HOXB4 - Induced Expansion of Adult Hematopoietic Stem Cells Ex Vivo," Cell, 109: 39-45, 2002.
Database Bios 'Online! Biosciences information service Philadelphia, PA, US; Nov. 16 2002 Krosl et al., "PBX1 Suppresses the Heamtopoietic Stem Cell Growth-Enhancing Effect of HoxB4", retrived from EPO, Database accession No. PREV200300335728, abstract.
Data Submitted in Corresponding EP application 2006755670, national entry date Jan. 14, 2008; published: Apr. 16, 2008.
Derossi et al., "Trojan peptides: The Penetratin System for Intracellular Delivery", Trends in Cell Biology, (1998) vol. 8: pp. 84-87.
Fischer et al., "Structure-activity Relationship of Truncated and Substituted Analogues of the Intracellular Delivery Vector Penetratin", J. Peptide Research (2000) vol. 55: pp. 163-172.
Fujino et al., "Inhbition of Myeloid Differentiation by Hoxa9, Hoxb8, and Meis Homeobox Genes", Experimental Hematology (2001) vol. 29: pp. 856-863.
Jiang et al., "Tumor imaging by means of proteolytic activation of cell-penetrating peptides", Proc Natl Acad Sci U S A. Dec. 21, 2004;101(51):17867-72. Epub Dec. 15, 2004.
Knoepfler et al., "HoxB8 Requires its Pbx-Interaction Motif to Block Differentiation of Primary Myeloid Progenitors and of Most Cell Line Models of Myeloid Differentiation" Oncogene (2001) vol. 20, pp. 5440-5448.
Knoepfler et al., "The Pentapeptide Motif of Hox Proteins Is Required for Cooperative DNA Binding with Pbx1, Physically Contacts Pbx1, and Enhances DNA Binding by Pbx1", Molecular and Cellular Biology (1995) vol. 15, No. 10, pp. 5811-5819.

(Continued)

*Primary Examiner*—David Lukton
(74) *Attorney, Agent, or Firm*—Fulbright & Jaworski, L.L.P.

(57) ABSTRACT

The present invention relates to peptides which impair PBX-dependent regulation of gene transcription. In particular, the invention provides the use of a peptide comprising the amino acid sequence $X_1 X_2 X_3$ W M $X_4 X_5 X_6 X_7$, wherein the sequence $X_1$ to $X_7$ is an amino acid sequence comprising at least 9 amino acids, which may optionally be interrupted by one or two amino acid residues between one or more of the 9 amino acid positions defined herein;

$X_1$ is selected from W, T, PE, KQI, VV, PQT, H, RI and absent;
$X_2$ is an amino acid with an aromatic side chain;
$X_3$ is P or D;
$X_4$ is an amino acid with a basic side chain;
$X_5$ is an amino acid with a charged side chain;
$X_6$ is an amino acid with a charged side chain; and
$X_7$ is an amino acid with a basic side chain or Serine;
in the manufacture of a medicament for treating or preventing a disorder in which aberrant cell division occurs.

12 Claims, 16 Drawing Sheets

OTHER PUBLICATIONS

Krosl et al., "Cellular proliferation and transformation induced by HOXB4 and HOXB3 Proteins Involves Cooperation with PBX1" Oncogne (1998) 16, pp. 3403-3412.

Lindgren et al., "Cell-Penetrating Peptides" TiPS (2000) vol. 21, pp. 99-103.

Lu et al. "Structural Determinants Within Pbx1 That Mediate Cooperative DNA Binding with Pentapeptide-Containing Hox Proteins: Proposal for a Model of a Pbx1-Hox-DNA Complex" Molecular and Cellular Biology (1996) vol. 16, pp. 1632-1640.

Medina et al., "In vivo mutagenesis of the Hoxb8 hexapeptide domain leads to dominant homeotic transformations that mimic the loss-of-function mutations in genes of the Hoxb cluster", Dev Biol. 2003 Dec. 1;264(1):77-90.

Morgan et al, "Identifying HOX Paralog Groups by the PBX-Binding Region" Trends in Genetics (2000) vol. 16: pp. 66-67.

Morgan et al., "Antagonism of HOX/PBX Dimer Formation Blocks the in vivo Proliferation of Melanoma", Cancer Res. Jun. 15, 2007;67(12):5806-13.

Morgan et al., "Pbx genes are required in Xenopus lens development", Int J Dev Biol. Sep. 2004;48(7):623-7.

Neuteboom et al., "The Hexapeptide LFPWMR in Hoxb-8 is Required for Cooperative DNA Binding with Pbx1 and Pbx2 Proteins" *Proc. Natl. Acad. Sci USA*, (1995) vol. 92, pp. 9166-9170.

Owens et al., "HOX and Non-HOX Homeobox Genes in Leukemic Hematopoiesis" Stem Cells, (2002) vol. 20, pp. 364-379.

Peltenburg et al., "Engrailed and Hox Homeodomain Proteins Contain a Related Pbx Interaction Motif that Recognizes a Common Structure Present in Pbx", The EMBO Journal, (1996) vol. 15, No. 13, pp. 3385-3393.

Persson et al., "Vesicle Membrane Interactions of Penetratin Analogues" Biochemistry (2004) vol. 43, pp. 11045-11055.

Phelan et al., "Cooperative Interactions between HOX and PBX Proteins Mediated by a Conserved Peptide Motif" Molecular and Cellular Biology (1995) vol. 15, No. 8: pp. 3989-3997.

Phelan et al., "Functional Differences between HOX Proteins Conferred by Two Residues in the Homeodomain N-Terminal Arm", Mol Cell Biol. Aug. 1994;14(8):pp. 5066-5075.

Shanmugam et al., "Residues Flanking the HOX YPWM Motif Contribute to Cooperative Interactions with PBX" The Journal of Biological Chemistry (1997), vol. 272(30): pp. 19081-19087.

Shen et al., "The Abd-B-like Hox Homeodomain Proteins Can Be Subdivided by the Ability to form Complexes with Pbx1 a on a Novel DNA Target", J Biol Chem. Mar. 28, 1997;272(13):8198-8206.

Shimamoto et al., "Homeobox Genes in Hematopoiesis and Leukemogenesis" International Journal of Hematology (1998), vol. 67: pp. 339-350.

Slupsky et al., "The HoxB1 Hexapeptide is a Prefolded Domain: Implications for the Pbx1/Hox Interaction" Protein Science (2001) vol. 10: pp. 1244-1253.

Sprules et al., "Conformational Changes in the PBX Homeodomain and C-Terminal Extension Upon Binding DNA and HOX-Derived YPWM Peptides" Biochemistry, (2000) vol. 39: pp. 9943-9950.

Sprules et al., "Lock and Key Binding of the HOX YPWM Peptide to the PBX Homeodomain" The Journal of Biological Chemistry, (2003) vol. 278: pp. 1053-1058.

Tanaka et al., "The Peptide Decoy for HOX Proteins Enhancs Ex Vivo Expansion of Human Umbilical Cord Blood Hematopoietic Stem Cells" Blood (2003) vol. 102: p. 183a Abstract #3079.

Thorén et al., "Uptake of Analogs of Penetratin, Tat (48-60) and Oligarginine in Live Cells" . Biochemical and Biophysical Research Communications (2003) vol. 307: pp. 100-107.

International Search Report issued Mar. 31, 2004 (published Jul. 1, 2004) during the prosecution of International Application No. PCT/GB2003/05425.

* cited by examiner

|  | 1 | 2 | 3 | 4 |
|---|---|---|---|---|
| BETA ACTIN | ++ | ++ | ++ | ++ |
| CD133 | ++ | ++ | - | ++ |
| CD38 | + | - | + | - |
| HOXB4 | + | + | - | + |
| HOXB8 | + | + | - | + |
| HOXA9 | + | + | - | + |
| TERT | ++ | ++ | + | + |
| CTCF | ++ | + | - | + |
| EIF4E | - | ++ | + | ++ |
| RAB27A | + | ++ | + | ++ |
| BAK2 | ++ | ++ | - | + |
| CDC25 | - | ++ | + | ++ |
| CDKN2 | + | ++ | + | ++ |
| MAPK | + | ++ | - | + |
| P53 | - | + | - | + |
| RAS-LKE | ++ | ++ | + | ++ |
| MMP1 | ++ | + | - | ++ |
| MMP19 | - | ++ | + | ++ |
| NRAS | + | ++ | - | ++ |

Figure 7b

|  | KG1a | | U937 | | HL60 | |
|---|---|---|---|---|---|---|
|  | C | H | C | H | C | H |
| BETA ACTIN | + | + | + | + | + | + |
| CD133 | ++ | + | - | - | - | - |
| CD34 | ++ | + | - | - | - | - |
| CD38 | + | ++ | + | ++ | + | ++ |
| HOXB4 | ++ | + | + | ++ | + | + |
| HOXB8 | ++ | + | + | + | + | + |
| HOXA9 | ++ | + | ++ | + | ++ | + |
| TERT | + | + | + | + | + | + |
| CTCF | ++ | ++ | ++ | ++ | ++ | ++ |
| EIF4E | + | + | + | + | + | + |
| RAB27A | + | + | + | + | + | + |
| BAK2 | + | + | + | + | + | + |
| CDC25 | - | - | ++ | + | + | + |
| CDKN2 | ++ | ++ | ++ | ++ | ++ | ++ |
| MAPK | + | + | + | + | + | + |
| P53 | + | + | + | + | + | + |
| RAS-LKE | ++ | ++ | ++ | ++ | ++ | ++ |
| MMP1 | + | - | + | - | - | - |
| MMP19 | ++ | + | - | - | - | - |
| NRAS | ++ | - | ++ | - | ++ | - |

Figure 9b

PEPTIDES IMPAIRING PBX DEPENDENT GENE REGULATION

CROSS-REFERENCE TO RELATED APPLICATIONS

This application is the National Stage of International Application No. PCT/GB03/05425 filed Dec. 12, 2003 which claims priority to Great Britain Application No. 0229151.6 filed Dec. 13, 2002.

TECHNICAL FIELD

The present invention relates to molecules which impair PBX-dependent transcription regulation, particularly peptides which affect the binding of HOX to PBX and their use in a number of applications, including the reduction of aberrant cell division, e.g. to treat certain cancers, and to maintain pluripotency of stem cells, e.g. to maintain the pluripotency of stem cells for example during culture expansion.

BACKGROUND OF THE INVENTION

A variety of transcription factors are involved in the regulation of expression of proteins during embryogenesis and adult stem cell maturation. Homeobox (HOX) genes contain a highly conserved nucleotide sequence of about 180 bp which encodes a homeodomain of about 60 amino acids. A homeodomain is a DNA-binding protein domain which can bind to target sequences in other genes and regulate their expression during development. The clustered Hox genes are key developmental regulators and are highly conserved throughout evolution. The homeotic HOX proteins which they encode share the 60 amino acid homeodomain and function as transcription factors to control axial patterning by regulating the transcription of subordinate downstream genes, e.g. developmental genes. In *Drosophila* and other insects there are eight different Hox genes that are encoded in two gene—complexes, while in vertebrates there are 39 genes organized in four complexes. The four gene complexes are assigned the letters A to D. Based on sequence similarities the genes can be sorted into 13 "paralog" groups. The order of the paralogs along the chromosomes are conserved in the four complexes. The gene name is obtained by concatenating the gene complex letter designation with the group number, e.g. HOXA1, HOXB4 etc.

Pre-B-cell transformation related gene (PBX) is also an important regulatory protein that controls gene expression during development by interacting cooperatively with HOX to bind to the target DNA (Mann et al., 1996, Trends Genet., 12(7), p 258-262). "Engrailed" proteins are also able to bind to PBX. PBX and HOX are known to interact via the hepta- or hexa-peptide region on the HOX molecule, which is highly conserved (Phelan et al., 1995, Mol. Cell. Biol., 15(8), p 3989-3997 and Neuteboom et al., 1995, PNAS, 92, p 9166-9170). The hexapeptide is separated by a linker region from the N-terminus of the homeodomain. Once PBX and HOX have bound to one another, they enter the nucleus of a cell and there bind to target DNA and repress or activate that target gene's transcription.

Whilst these proteins are known to be involved in embryogenesis their precise roles have not been elucidated. Over or under expression of HOX proteins gives rise to a variety of consequences in vitro which implicate the involvement of these proteins in the control of differentiation processes. However the consequences of perturbing the interaction between PBX and the co-factors to which it binds have not been examined. Furthermore, PBX:HOX binding antagonists have been found to be rather specific to specific forms of the protein binding partners involved (see Peltenburg & Murre, 1996, EMBO Journal, 15(13), p. 3385-3393). Furthermore, it is believed that the linker region between the homeobox and the hexapeptide is required for cooperative binding between PBX and HOX (Peltenburg & Murre, supra and Neuteboom et al., 1995, PNAS, 92, p 9166-9170).

BRIEF SUMMARY OF THE INVENTION

The present inventors have now developed a peptide which mimics the region of HOX to which PBX binds and acts as an antagonist of that binding. This peptide is based on the hexapeptide region of HOXB-4 but has been found to have cross-reactivity (see Example 2) and reduces the binding of PBX to all HOX proteins. This is the first report of a peptide having such global PBX:HOX effects. Furthermore, unlike other HOX-interacting peptides, the peptide of the present invention does not contain a linker region.

It has also been found that inhibiting the binding of PBX to its binding partners has profound and useful effects on stem cells, which allows the pluripotency of these cells to be maintained. It has also been found that as a converse effect, aberrant cell growth may be reduced to prevent or treat disorders or conditions in which such cell growth occurs. These findings offer significant clinical applications in which desired cells may be protected and possibly expanded whilst the growth of detrimental cells may be prevented.

Accordingly, the invention provides the use of a peptide comprising the amino acid sequence $X_1 X_2 X_3 W M X_4 X_5 X_6 X_7$ wherein the sequence $X_1$ to $X_7$ is an amino acid sequence comprising at least 9 amino acids, which may optionally be interrupted by one or two amino acid residues between one or more of the 9 amino acid positions defined herein;

$X_1$ is selected from W, T, PE, KQI, VV, PQT, H, RI and absent;

$X_2$ is an amino acid with an aromatic side chain;

$X_3$ is P or D;

$X_4$ is an amino acid with a basic side chain;

$X_5$ is an amino acid with a charged side chain;

$X_6$ is an amino acid with a charged side chain; and $X_7$ is an amino acid with a basic side chain or Serine;

in the manufacture of a medicament for treating or preventing a disorder in which aberrant cell division occurs.

In one embodiment, the peptide may further comprise a cell penetration moiety. Particularly preferred peptides are:

W Y P W M K K H H R Q I K I W F Q N R R M K W K,
W Y P W M K K H H R Q I K I W F Q N R R M K W K K, and
W Y P W M K K H H R.

The disorder to be treated is preferably a cancer. The cells to be treated preferably express one or more Hox genes.

The invention also provides:

use of a peptide of the invention and a cytotoxic or chemotherapeutic agent in the manufacture of a medicament for simultaneous, sequential or separate use in the treatment or prevention of a disorder in which aberrant cell division occurs.

use of a peptide of the invention in the manufacture of a medicament for reducing the side effects of a cytotoxic or chemotherapeutic agent.

use of a peptide of the invention in the manufacture of a medicament for maintaining or expanding a stem cell population in vivo.

a method of treating a disorder in which aberrant cell division occurs in a human or animal comprising administering to said human or animal a therapeutically effective amount of a peptide of the invention.

a method of maintaining or expanding stem cells ex vivo comprising contacting said stem cells with a peptide of the invention. Such a method may further comprise the step of culturing said cells in the absence of said peptide, and/or administering said stem cells to a patient in need thereof. Stem cells that have been maintained or expanded by such a method also form an aspect of the invention.

use of a stem cell of the invention in the manufacture of a medicament for the treatment or prevention of a condition resulting in a decreased level of stem cells.

a pharmaceutical composition comprising a peptide of the invention and a pharmaceutically acceptable carrier.

DETAILED DESCRIPTION OF THE INVENTION

Figure 1:
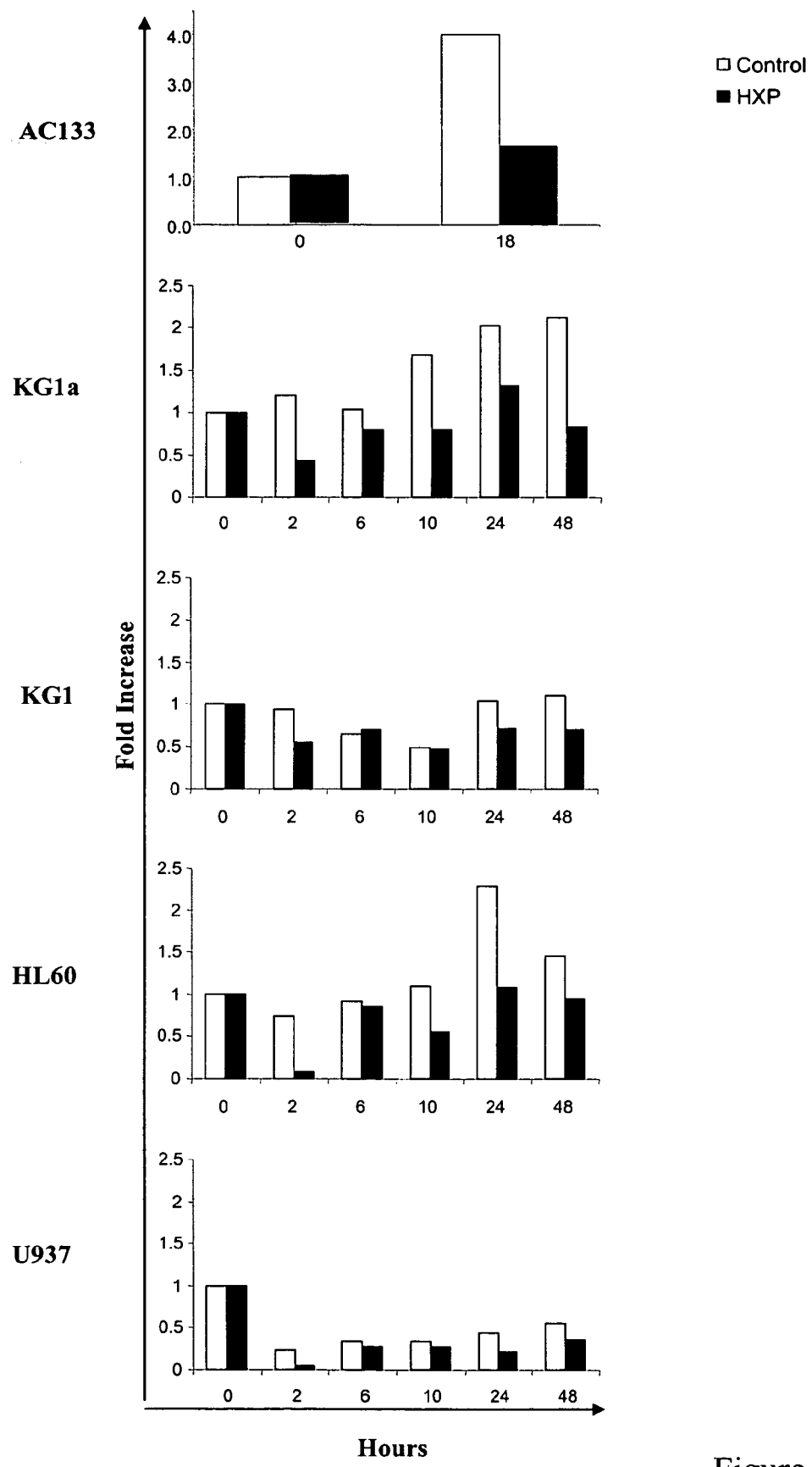
FIG. 1 shows the effect of HXP peptide on cell growth of immature blood stem cells (AC133+ cells) and on leukaemic cell lines KG1a, KG1, HL60 and U937 as a function of the time after HXP administration.
Figure 2:
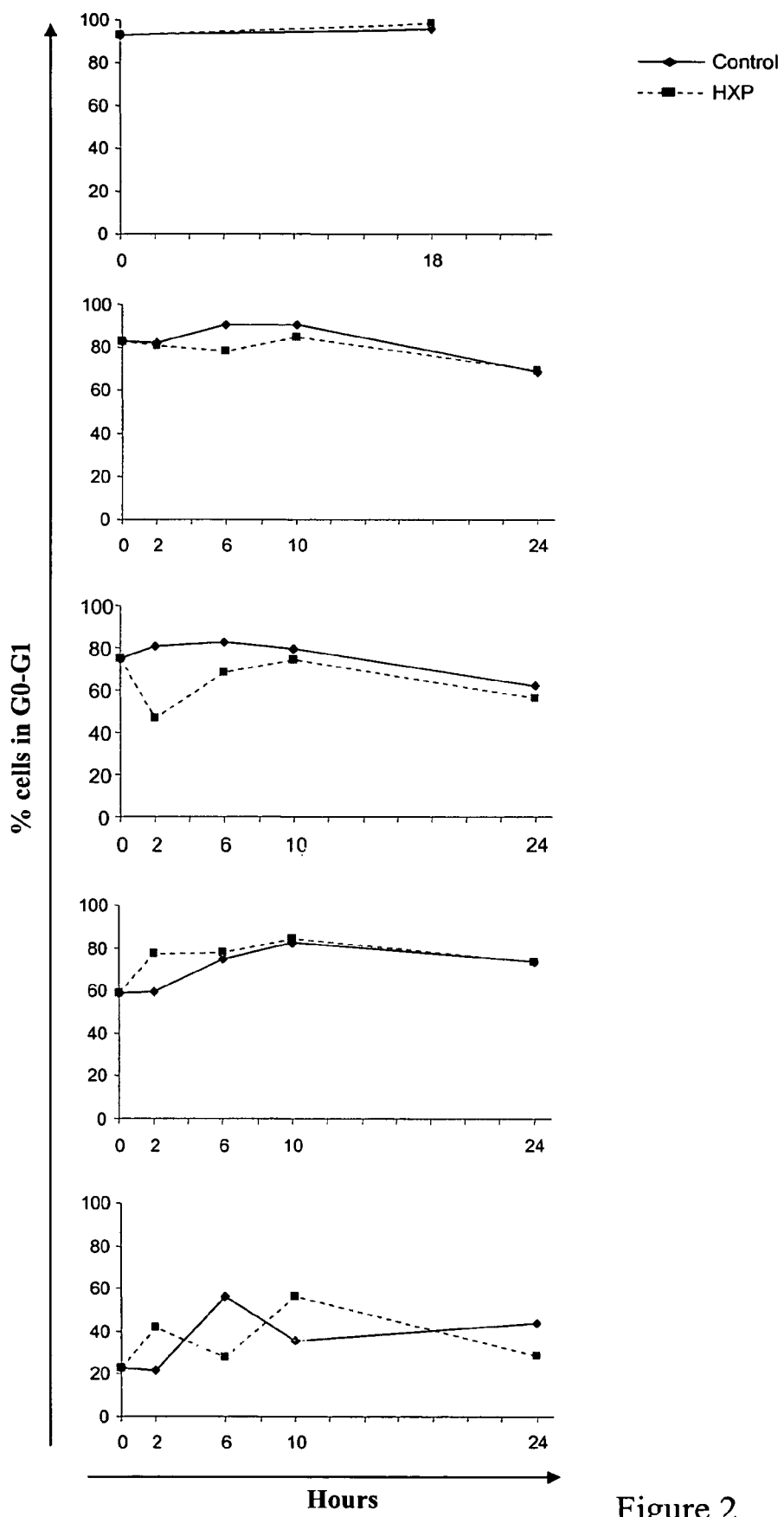
FIG. 2 shows the effect of HXP peptide on the cell cycle of cells (AC133+, KG1a, KG1, HL60 and U937) to which it is administered as a function of the time after HXP administration.

The present invention relates to molecular mimics of the HOX hexapeptide region. It is now shown that molecules which impair PBX-dependent transcription regulation (e.g. activation or repression), e.g. by interfering with the interaction between PBX and its co-factors, preferably HOX, and its target DNA, e.g. molecules which affect the binding of HOX and PBX proteins, have downstream effects which can offer great advantages such as preventing or reducing aberrant cell division and maintaining pluripotency of stem cells.

Preferred PBX modulators are peptides. "Peptides" as referred to herein are molecules with less than 100 amino acid residues, but are preferably shorter, e.g. less than 50, e.g. less than 30 residues in length, preferably from 8 to 25 residues in length.

Preferred peptides of the invention have the general formula (I) (SEQ ID NO: 1):

$$Y_1\text{-}X_1\text{-}X_2\text{-}X_3\text{-}W\text{-}M\text{-}X_4\text{-}X_5\text{-}X_6\text{-}X_7\text{-}Y_2 \quad (I)$$

wherein the sequence $X_1$ to $X_7$ is an amino acid sequence comprising at least 9 amino acids, which may optionally be interrupted by one or more (preferably one or two) amino acid residues between one or more of the 9 amino acid positions defined herein;

$Y_1$, which may be present or absent, is a moiety attached to $X_1$ (or $X_2$ when $X_1$ is absent) preferably via the available amino group on $X_1$ (or $X_2$), but alternatively via the side-chain of $X_1$ (or $X_2$), wherein $Y_1$ is preferably a peptide of 50 amino acids or less which is optionally substituted;

$Y_2$, which may be present or absent, is a moiety attached to $X_7$, preferably via the carboxyl group on $X_7$, but alternatively via the side-chain of $X_7$, wherein $Y_2$ is preferably a peptide of 50 amino acids or less which is optionally substituted;

$X_1$, which may be present or absent, is one or more amino acids, and is preferably W, T, PE, KQI, UV, PQT, H or RI;

$X_2$ is an amino acid with an aromatic side chain, preferably Y, F or W;

$X_3$ is the amino acid P or D;

$X_4$ is an amino acid with a basic side chain, preferably K, R or H;

$X_5$ is an amino acid with a charged side chain, preferably a basic side chain, especially preferably K, R, E, H, D, N or Q;

$X_6$ is an amino acid with a charged side chain, preferably a basic side chain, especially preferably K, R, E, H, D, N or Q $X_7$ is an amino acid with a basic side chain or serine, especially preferably H, S, R or K;

or a functionally equivalent derivative, variant or fragment thereof.

As mentioned above, $Y_1$ and/or $Y_2$ may be substituted by a further moiety. Such moieties may be added to aid the function of the peptide, its targeting or its synthesis, capture or identification, e.g. a label (e.g. biotin) or lipid molecules.

In one embodiment $Y_1$ and/or $Y_2$ may therefore be absent or be further amino acid sequences. That is, a peptide of the invention may comprise the general formula (SEQ ID NO: 2): $X_1\text{-}X_2\text{-}X_3\text{-}W\text{-}M\text{-}X_4\text{-}X_5\text{-}X_6\text{-}X_7$ wherein $X_1$ to $X_7$ are defined as above.

In the above sequence, $X_1$ to $X_4$ forms the hexapeptide sequence.

Preferred peptides of formula I, have the formula Ia (SEQ ID NO: 3):

wherein $Y_1$, $X_1$ and $Y_2$ are as defined hereinbefore

Especially preferably formula Ia has the sequence (Ib) (SEQ ID NO: 4):

especially preferably $Y_1$ W Y P W M K K H H $Y_2$ (SEQ ID NO: 5) wherein $Y_1$, $X_1$ and $Y_2$ are as defined hereinbefore.

Particularly preferred peptides have or comprise the amino acid sequence

```
WYPWMKKHH       (SEQ ID NO: 6)
OR

WYPWMKKHHR.     (SEQ ID NO: 7)
```

A peptide of the invention may comprise a cell penetration moiety, wherein said moiety is preferably a peptide, which may optionally be substituted, e.g. with a label or attachment moiety.

As used herein a "cell penetration moiety" refers to a molecule, structure or collection of molecules which assist or facilitate entry of the molecule to which it is attached into a cell. A variety of such moieties are well-known in the art and include peptides such as penetratins, tat-derived proteins, peptide signal sequences that allow cell entry, peptides comprising such peptide signals as well as synthetic and/or chimeric cell-penetrating peptides such as transportan or model amphipathic peptides (Lindgren et al., 2000, TiPS, 21, p 99-103 and Derossi et al., 1998, Trends C. Biol., 8, p 84-87). Non-peptide molecules or substances which are capable of entering cells may also be used. Preferably said cell penetration moiety acts by a receptor-independent mechanism. Any substance that can allow or help a molecule, such as a peptide of the invention, to enter a cell may be used. The moiety may be a generally acting substance that can enter a variety of cell types, or may be specific or targeted to a particular cell type to be treated.

In a preferred embodiment, such a cell penetration moiety will be found at the carboxy-terminal of a peptide as defined in any one of SEQ ID NOs: 1 to 7. A cell penetration moiety may be directly linked to the carboxy terminal of such a peptide. In a peptide of formula (I), (Ia) or (Ib), $Y_2$ may be, or may comprise, a cell penetration moiety. A cell penetration moiety may alternatively be associated with a peptide of general formula (I), e.g. may encapsulate or form a complex with said peptide, e.g. by using liposomes for lipofection or polycations or cationic lipids. "Associated with" as used herein refers to the moiety being attached to, or connected in some way, to the peptide.

In a preferred feature said cell penetration moiety is a peptide based on the penetratin sequence and has the following general formula II (SEQ ID NO: 8):

$X_8$QIKIWFQNKWKK    (II)

wherein $X_8$ is the amino acid R or Q, or a functionally equivalent derivative, variant or fragment thereof.

Preferably a variant of the formula II sequence is a peptide in which one or more of said K residues in the formula II sequence is replaced with an R residue, one or more of said R residues in the formula II sequence is replaced with a K residue and/or one or more of said I residues in the formula II sequence is replaced with an L residue.

That is, a cell penetration moiety of the invention may be defined by the general formula:

$X_8$ Q $X_9$ $X_{10}$ $X_{11}$ W F Q N $X_{12}$ $X_{13}$ M $X_{14}$ W $X_{15}$ $X_{16}$    (SEQ ID NO: 9)

wherein $X_8$ is R or Q or absent;

$X_9$, $X_{11}$ are each independently I or L; and $X_{10}$, $X_{12}$, $X_{13}$, $X_{14}$, $X_{15}$ and $X_{16}$ are each independently K or R.

Especially preferably, said variant has the form:

```
QIRIWFQNRRMKWKK;     (SEQ ID NO: 10)
QIKIWFQNKRMKWKK;     (SEQ ID NO: 11)
QIKIWFQNKKMKWKK;     (SEQ ID NO: 12)
QIRIWFQNRKMKWKK;     (SEQ ID NO: 13)
QIRIWFQNRRMRWKK;     (SEQ ID NO: 14)
QIRIWFQNRRMKWRK;     (SEQ ID NO: 15)
QIRIWFQNRRMKWKR;     (SEQ ID NO: 16)
QIRIWFQNRRMKWRR;     (SEQ ID NO: 17)
QIRIWFQNRRMKWKK;     (SEQ ID NO: 18)
QIKIWFQNRRMKWRK;     (SEQ ID NO: 19)
QIRIWFQNKRMKWRK;     (SEQ ID NO: 20)
QIKLWFQNRRMKWKK,     (SEQ ID NO: 21)
QLKLWFQNRRMKWKK;     (SEQ ID NO: 22)
or
QLRIWFQNRRMKWKK.     (SEQ ID NO: 23)
```

Preferably the peptide of formula II forms the $Y_2$ group of the peptides of formula I or Ia.

The present invention relates in particular to peptides having the following sequence:

WYPWMKKHHR    (SEQ ID NO: 7)

or functionally equivalent derivatives, variants or fragments thereof.

This peptide may be further attached to a cell penetration moiety as defined above in SEQ ID NO: 9

A particularly preferred peptide has the sequence

WYPWMKKHHRQIKIWFQNRRMKWKK,    (SEQ ID NO: 24)

or a functionally equivalent derivative, variant or fragment thereof.

"Functionally equivalent" derivatives, variants or fragments thereof refers to peptides related to, or derived from the amino acid sequence of SEQ ID NOs: 7 or 24, where the amino acid sequence has been modified by for example the use of modified amino acids or by single or multiple amino acid (e.g. at 1 to 10, e.g. 1 to 5, preferably 1 or 2 residues) substitution, addition and/or deletion but which nonetheless retain functional activity, insofar as they act as HOX mimics and thus antagonize the interaction between HOX proteins and PBX proteins (preferably PBX1 or PBX2) according to the assay described hereinafter (see Example 2, in which cross-linking of large molecules indicative of HOX:PBX binding is not observed).

Preferred functionally equivalent derivatives, variants or fragments of the peptides of SEQ ID Nos: 7 and 24 will fall within the scope of or comprise the sequence of SEQ ID NO: 1, or SEQ ID NO: 1 wherein $Y_2$ is or comprises SEQ ID NO: 9.

Within the meaning of "addition" variants are included amino and/or carboxyl terminal fusion proteins or polypeptides, comprising an additional protein or polypeptide fused to the peptide sequence.

"Substitution" variants preferably involve the replacement of one or more amino acids with the same number of amino acids and making conservative substitutions.

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the peptide is not significantly adversely affected.

Derivatives and variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

Functionally-equivalent "fragments" according to the invention may be made by truncation, e.g. by removal of a peptide from the N and/or C-terminal ends. Such fragments may be derived from a sequence of SEQ ID NO: 1 (optionally together with SEQ ID NO: 9) or may be derived from a functionally equivalent peptide as described above. Preferably such fragments are between 6 and 30 residues in length, e.g. 6 to 25 or 10 to 15 residues.

Preferably functional variants according to the invention have an amino acid sequence which has more than 70%, e.g. 75 or 80%, preferably more than 85%, e.g. more than 90 or 95% homology to SEQ ID NO: 7 or 24, (according to the test described hereinafter).

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Peptides of the invention, as defined herein, may be chemically modified, for example, post-translationally modified. For example they may be glycosylated or comprise modified amino acid residues. They can be in a variety of forms of polypeptide derivatives, including amides and conjugates with polypeptides.

Chemically modified peptides also include those having one or more residues chemically derivatized by reaction of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine.

Also included as chemically modified peptides are those which contain one or more naturally occurring amino acid derivatives of the twenty standard amino acids. For example, 4-hydroxyproline may be substituted for proline or homoserine may be substituted for serine.

A peptide of the invention may carry a revealing label. Suitable labels include radioisotopes such as $^{125}$I, $^{32}$P or $^{35}$S, fluorescent labels, enzyme labels, or other protein labels such as biotin.

Peptides as described above for use in accordance with the invention may be prepared by conventional modes of synthesis including genetic or chemical means. Synthetic techniques, such as a solid-phase Merrifield-type synthesis, may be preferred for reasons of purity, antigenic specificity, freedom from unwanted side products and ease of production. Suitable techniques for solid-phase peptide synthesis are well known to those skilled in the art (see for example, Merrifield et al., 1969, Adv. Enzymol 32, 221-96 and Fields et al., 1990, Int. J. Peptide Protein Res, 35, 161-214). Chemical synthesis may be performed by methods well known in the art involving cyclic sets of reactions of selective deprotection of the functional groups of a terminal amino acid and coupling of selectively protected amino acid residues, followed finally by complete deprotection of all functional groups.

Synthesis may be performed in solution or on a solid support using suitable solid phases known in the art.

In an alternative embodiment a peptide of the invention may be produced from or delivered in the form of a polynucleotide which encodes, and is capable of expressing, it. Such polynucleotides can be synthesised according to methods well known in the art, as described by way of example in Sambrook et al (1989, Molecular Cloning—a laboratory manual; Cold Spring Harbor Press). Such polynucleotides may be used in vitro or in vivo in the production of a peptide of the invention. Such polynucleotides may therefore be administered or used in the manufacture of a medicament for the treatment of cancer or another disease or condition as described herein.

The present invention also includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, the peptide may be provided by delivering such a vector to a cell and allowing transcription from the vector to occur. Preferably, a polynucleotide of the invention or for use in the invention is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters, such as b-actin promoters, may be used. Tissue-specific promoters are especially preferred. Mammalian promoters include the metallothionein promoter which can be induced in response to heavy metals such as cadmium. Viral promoters may also be used, for example the SV40 large T antigen promoter, adenovirus promoters, the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). All these promoters are readily available in the art.

The invention also includes cells that have been modified to express a peptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors encoding for a peptide of the invention include mammalian HEK293T, CHO, HeLa and COS cells. Preferably the cell line selected will be one which is not only stable, but also allows for mature glycosylation and cell surface expression of a polypeptide. Expression may be achieved in transformed oocytes. A suitable peptide may be expressed in cells of a transgenic non-human animal, preferably a mouse. A transgenic non-human animal expressing a peptide of the invention is included within the scope of the invention. A peptide of the invention may also be expressed in *Xenopus laevis* oocytes or melanophores.

The present invention also extends to antibodies (monoclonal or polyclonal) and their antigen-binding fragments (e.g. F(ab)2, Fab and Fv fragments i.e. fragments of the "variable" region of the antibody, which comprises the antigen binding site) directed to peptides as defined hereinbefore, i.e. which bind to epitopes present on the peptides and thus bind selectively and specifically to such peptides, and which may be used in the methods of the invention.

The peptides of the invention, as described above, are able to specifically block the interaction between PBX and HOX. As shown in the Examples, peptides of the invention have been found to block the growth of, or in some circumstances completely ablate, a wide range of cancer cell types. Accompanying these changes, down-regulation of a number of known HOX targets is observed. As described in more detail below, the peptides of the invention may therefore have therapeutic uses in the treatment of cancers in which Hox genes are expressed, as cytoprotective agents during other cancer therapies or in the ex vivo protection of stem cell cultures.

Peptides described above may be used to block interactions of PBX with its binding partners, e.g. HOX, and preferably thereby prevent the binding of HOX to its target DNA. Thus in a further aspect the present invention provides use of a peptide as described hereinbefore to reduce or inhibit binding of PBX to a binding partner, preferably HOX, or the use of such peptides to reduce or inhibit binding of HOX to its target DNA.

"PBX" refers to the family of pre-B-cell transformation related genes and includes genes encoding extradenticle homeoprotein proteins and homologues of the *Drosophila* extradenticle gene, such as genes in vertebrates. Vertebrate PBX proteins are transcription factors that contain a homeodomain (Mann et al., 1996).

"HOX" refers to homeobox genes which contain a sequence which encodes a homeodomain of about 60 amino acids and a sequence which encodes the hexapeptide sequence N-terminal to the homeodomain (Morgan et al., 2000, TIG, 16{2}, p 66-67 and Krumlauf, 1994, Cell, 78 {2}, p 191-201). The HOX proteins are transcription factors that act to define anterior-posterior development in early development. Such PBX or HOX genes or proteins as described herein include homologues present in any multicellular animal, but are preferably from vertebrates, e.g. from mammals, especially preferably from humans.

As referred to herein "binding" refers to the interaction or association of at least two moieties in a reversible or irreversible reaction, wherein said binding is preferably specific and selective.

As used herein a "binding partner" refers to a molecule which recognizes and binds specifically (i.e. in preference to binding to other molecules) to its binding partner. Such binding pairs when bound together form a complex.

A "reduction in binding" refers to a decrease in binding, e.g. as manifest by an increased concentration of one of the binding pair required to achieve binding. Reduction includes a slight decrease as well as absolute abrogation of specific binding. A total reduction of specific binding is considered to equate to a prevention of binding. "Inhibition" refers to competitive interference of the binding of the binding partners by the peptide, which serves to reduce the partners' binding.

Agents which prevent or reduce PBX-dependent transcription regulation, have surprisingly been found to have advantageous effects on aberrant cell division as described herein. Such agents are preferably those which prevent, reduce or inhibit the binding of PBX to its binding partners, especially preferably the binding between PBX and HOX (such as antagonists of the interaction between HOX and PBX, e.g. the peptides described hereinbefore). However, suitable agents also include those that affect binding of the transcription factors to the target DNA, e.g. which block the interaction of PBX or its binding partner, such as HOX, to the target DNA. Especially preferably such agents prevent HOX-dependent transcription regulation.

Whilst not wishing to be bound by theory, it is believed that antagonists of HOX:PBX binding prevent the interaction between multiple important HOX:PBX protein binding partners, and the HOX proteins are therefore unable to act as transcription factors on the genes to which they bind. The failure to regulate expression of these genes may have numerous effects on the cells, for example reducing or preventing the excessive cell division. Similarly any moiety which prevents or reduces PBX-dependent transcription regulation, e.g. blocks the interaction of HOX with its target DNA, may be expected to have similar effects.

In a further aspect, therefore, the present invention provides a method of reducing aberrant cell division wherein said cells are administered an agent which prevents or reduces PBX-dependent transcription regulation, preferably which reduces or prevents binding of PBX to a binding partner, preferably to HOX (preferably HOXB4, HOXB8 or HOXA9) or reduces or prevents binding of HOX to its target DNA, preferably an antagonist, especially preferably an antagonist of the interaction between HOX and PBX, especially preferably a peptide as described herein (and which preferably inhibits HOX-dependent transcription regulation).

Agents which are suitable for this purpose include antagonists of the interaction between HOX and/or PBX and the DNA target to which they bind, antagonists of the interaction between PBX and its binding partners, especially HOX proteins, or agents which impair the binding ability of HOX/PBX or the target DNA, e.g. which block relevant sites or cause structural changes at relevant sites on HOX/PBX or the target DNA or reduce the number of molecules available for binding (which may be achieved by for example modifying the expression/expressed product of PBX/HOX). Preferably however, antagonists are employed. Preferred agents are the peptides of the invention as described above.

As described herein, "aberrant cell division" refers to cell division above the normal level (i.e. abnormal cell division) considered appropriate under the conditions which exist. Markers of aberrant cell division are well known to the person skilled in the art and can be used to determine whether a particular cell has been effected. For example, cells undergoing aberrant cell division may show atypical cytology, for example cellular pleomophism, nuclear pleomorphism, nuclear hyperchromatism or an increased nuclear:cytoplasmic ratio. Cells undergoing aberrant cell division may show a failure of cell differentiation. More particularly, such aberrant cell division may be present in certain conditions or diseases/disorders as described hereinafter, such as cancer.

"Reducing" cell division refers to reducing the rate of cell growth. Preferably cell growth is reduced to less than 0.5, especially preferably less than 0.25, e.g. less than 0.1 relative to control growth (without the agent) over the same time period (wherein control growth=1). In a preferred aspect reduced cell division encompasses cell death/lack of viability which may occur in addition, or as an alternative to the reduction in cell growth. When cell death occurs preferably more than 50% of the existing cells, preferably more than 75% of the cells are destroyed.

As shown in the Examples, by increasing the dose of the agent used it is also possible to completely ablate some malignancies. Peptides of the invention may therefore be used to slow the growth of, or completely destroy, cancerous cells. As explained in more detail below, a suitable dose will depend on a number of factors and can be determined by a skilled practitioner.

As described herein "PBX-dependent transcription regulation" refers to activation or suppression of the transcription of genes by processes in which PBX plays a pivotal role, e.g. acts as a cofactor in the transcription regulatory complexes. Prevention or reduction refers to a measurable change in the extent of transcription. Prevention equates to a reduction in transcription to undetectable levels.

"Target DNA" refers to the gene containing the regulatory region to which PBX, HOX or any member of the transcription regulation complex containing such proteins, binds. As referred to herein, an "antagonist" is a molecule or complex of molecules which by virtue of structural similarity to one molecule of a binding pair competes with that molecule for binding to the other molecule of the binding pair. Antagonists for use in the invention include antagonists of the interaction between HOX and PBX which prevent or reduce binding between those entities. Preferred antagonists are peptides, antibodies, or anti-idiotypes in which these molecules bind to, or compete with the binding site on HOX or PBX. Preferably the antagonists compete by mimicking the PBX binding site on HOX, ie. binding to PBX, e.g. peptides as described hereinbefore.

Other antagonists include those which prevent or reduce binding between HOX and its target DNA. HOX proteins are known to bind to a 6 base pair consensus sequence NNATTA on their target DNA and antagonists of this binding, e.g. oligonucleotides which are complementary to that sequence (e.g. sets of oligonucleotides with variability at 2 bases to accommodate the variability in the consensus sequence described above) are suitable as agents for the above described purpose.

Such methods may be performed in vitro, in vivo or ex vivo. Conveniently such methods are performed in vivo by the administration of said agent, preferably an antagonist as described hereinbefore, to a human or non-human animal to treat or prevent a condition or disorder in which aberrant cell division occurs, e.g. cancer or a non-cancerous growth such as myelodysplastic syndrome (MDS). Alternatively expressed, the present invention provides the use of an agent as described hereinbefore, preferably an antagonist, especially preferably an antagonist of the interaction between HOX and PBX, e.g. a peptide as described hereinbefore, in the manufacture of a medicament for the treatment or prevention of a condition or disorder in which aberrant cell division occurs.

As referred to herein a "disorder" or a "disease" refers to an underlying pathological disturbance in a symptomatic or asymptomatic organism relative to a normal organism, which may result, for example, from infection or an acquired or congenital genetic imperfection.

A "condition" refers to a state of the mind or body of an organism which has not occurred through disease, e.g. the presence of a moiety in the body such as a toxin, drug or pollutant.

As defined herein "treatment" refers to reducing, alleviating or eliminating one or more symptoms of the condition or disorder which is being treated, relative to the symptoms prior to treatment. Treatment encompasses improving the condition of a patient having or suffering from the condition or disorder to be treated. For example, symptoms which may be affected include tumour size or numbers of cancerous cells in a given sample (or reduced stem cell numbers as described hereinafter).

"Prevention" of a condition or disorder refers to delaying or preventing the onset of a condition or disorder or reducing its severity, as assessed by the appearance or extent of one or more symptoms of said condition or disorder.

As an alternative to performing the methods in vivo, such methods may be performed in vitro, e.g. to reduce the cell division of, or eliminate, cells undergoing aberrant cell growth, in a sample. Appropriate culture conditions are as described for other methods of the invention as described hereinafter.

This is particularly useful in cell samples containing both normal and aberrant cells in which aberrant cells may be controlled/removed and the sample containing the normal cells used for subsequent procedures, e.g. returned to the donor body. This may be useful to, for example, eliminate aberrant haematopoietic blood cells from a blood sample of a patient, e.g. leukaemic cells, and the remaining cells may then be returned to the body of that patient.

Thus in a yet further aspect the present invention provides a method of reducing aberrant cell division (preferably of reducing the growth, preferably involving the death and hence reducing the number, of cancer cells) in cells in a sample, wherein an agent as described hereinbefore is administered to said sample. In a method for treating patients suffering from a disorder or condition typified by aberrant cell division (or preventing the same), said sample may be harvested from said patient and then returned to that patient as described hereinafter. In this context, a "sample" refers to any material obtained from a human or non-human animal, including embryonic, foetal, immature and adult stages of said animal, which contains cells undergoing aberrant cell division and include tissues and body fluids. "Body fluids" in this case include in particular blood, spinal fluid and lymph and "tissues" include tissue obtained by surgery or other means.

Preferably the aberrant cell division occurs in cells from eukaryotic organisms which may be any eukaryotic organisms such as human beings, other mammals and animals, birds, insects and fish.

Preferred non-human animals from which cells may be derived or on which methods of the invention may be conducted include, but are not limited to mammals, particularly primates, domestic animals, livestock and laboratory animals. Thus preferred animals include mice, rats, chickens, frogs, guinea pigs, cats, dogs, pigs, cows, goats, sheep, horses. Particularly preferably the cells are derived from, and the methods used to treat, or be prophylactic in, humans.

Preferably the cells undergoing aberrant cell division are cancer cells and the disorder to be treated or prevented is a cancer. Cancers that can be treated in this way are those cancers which involve the expression of HOX genes, wherein this HOX expression is reduced by the activity of a peptide of the invention, thus blocking the growth of, reducing the proliferation of, or leading directly to the death of, the cancerous cells. In a further embodiment, as described in more detail below, the peptide of the invention may act on the cancerous cells to move them from a quiescent state into the cell cycle and thus make them more susceptible to other, e.g. cytotoxic, anti-cancer treatments.

Preferably said cell to be treated expresses one or more Hox genes. For example, said cell may express one or more of HOXA1, HOXA3, HOXA4, HOXA5, HOXA7, HOXA9, HOXA11, HOXA13, HOXB1, HOXB2, HOXB3, HOXB4, HOXB8, HOXB9, HOXB13, HOXC4, HOXC6, HOXC8, HOXC10, HOXD3, HOXD4, HOXD8, HOXD9, HOXD10 and HOXD13. Said cell may express one or more of HOXB4, HOXB8 and HOXA9. It is possible that the level of Hox gene expression in the cell may be directly related to the sensitivity of the cell to the peptides of the invention. The peptides of the invention would therefore be more effective at treating cells which show high levels of HOX gene expression, for example higher levels of HOX gene expression than that in the surrounding tissue or higher levels of HOX gene expression than that of other cancer types where the cell is a cancer cell. The methods of the invention may therefore be particularly suitable where the cells to be treated show such increased or higher levels of Hox gene expression.

Preferably said cancers are malignant or pre-malignant or benign tumours and include carcinomas, sarcomas, gliomas, melanomas and lymphomas, including cancers of the bladder, kidney, pancreas, brain, head and neck, breast, gut, prostate, lung and ovary and leukaemias and lymphomas. Particularly preferred are colorectal, pancreatic, bladder, prostate, cervical, ovarian, gastric and small cell lung cancers.

Thus in a preferred aspect, the present invention provides a method of treating or preventing cancer, in a human or non-human animal wherein said animal is administered an agent, preferably an antagonist, as described hereinbefore.

In some cancers, for example some forms of human pre-B cell leukaemia, PBX may act as an oncogene. The effects of PBX in such cancers will be different to that in other cancer types where PBX is not an oncogene. The effects of a peptide mimic of the invention will also therefore be different. In one embodiment, therefore, the present invention does not apply to such cancers because the effect of a peptide of the invention will be via a different mechanism to the PBX:HOX effect elucidated by the inventors. In this embodiment, therefore, a peptide of the invention may be used in the treatment or prevention of a cancer or other disorder in which aberrant cell division occurs, that expresses one or more Hox genes, and in which PBX does not act as an oncogene. For example, a suitable cancer for treatment by a method of the invention may be a leukaemia other than human pre-B cell leukaemia.

In some cancers, such as acute myeloid leukaemia (AML), the peptides of the invention have been shown to block the proliferation of the cancerous cells, but are also stimulated to leave the G0/G1 quiescent state and enter the cell cycle. These two effects are seen in the same cells under the same conditions. This is likely to be due to the cells being triggered to leave G0/G1 by the peptide (i.e. enter the cell cycle) but then failing to divide and instead either differentiating or undergoing apoptosis. As shown in the Examples, the effects of the peptides of the invention in AML cells is not dependent on the stage of development at which the cell line is arrested. The peptides of the invention may therefore be used in the treatment of both primary AML and mature myeloid leukaemias. This suggests a specific utility for the peptides of the invention in acute myeloid and lymphoid leukaemias. Blocking PBX/HOX interactions in these cells using a peptide of the invention may therefore form an effective treatment for preventing leukaemia cell growth in vivo. In addition, by increasing the proportion of leukaemic cells that enter the cell cycle, the peptides of the invention may also increase their sensitivity to other cancer treatments such as chemotherapy.

Agents which prevent or reduce PBX-dependent transcription regulation have also been found to have beneficial effects on stem cells.

"Stem cells" as referred to herein are undifferentiated cells which are capable of differentiating into various cells, e.g. various blood cell types, and include haematopoietic (e.g. found in the bone marrow) and neural and hepatic stem cells, embryonic stem cells and embryonic germ cells and encompass both pluri- and toti-potent cells. Embryonic cells are considered to be those cells derived from the inner cell mass of the blastocyst and embryonic germ cells are those cells isolated from the primordial germ cell of the gonadal ridge of the 5 to 10 week old foetus. Preferably said cells are derived from eukaryotic organisms as described previously.

As described in the Examples herein, it has now been found that prevention of PBX-mediated transcription regulation results in reduced, but continued, cell division and the appearance of molecular markers of differentiation (e.g. CD38). However on removal of the agent blocking that transcriptional regulation cells reverted to stem cells as assessed by the appearance of molecular markers (e.g. HOXB4, HOXB8, HOXA9, AC133), thus reflecting pluripotency of the cells. Whilst not wishing to be bound by theory, it is believed that despite the appearance of markers of differentiation/maturation, no phenotypic changes symptomatic of differentiation occur and the cells instead have a significantly reduced rate of cell cycling while the agent is being administered. On removal of the agent, the cells revert to stem cells.

It is also now shown that treatment of pluripotent haematopoietic stem and progenitor cells (HSPCs) with a peptide of the invention blocks their proliferation, and increases the proportion of cells in the G0-G1 phase of the cell cycle. The longevity of the cultures confirms the effects of putative stem cells as well as more differentiated progenitor populations. The specificity of this inhibitory effect of peptides of the invention on these gene targets is underlined by its reversibility, with gene transcription and cell growth resuming on removal of the peptide.

These results have a number of applications which include maintenance or expansion of stem cells (e.g. in culture), for example for temporary storage of said cells, with possible expansion during that storage period. Such cells may then, for example, be used in clinical applications in which the addition of stem cells is desirable, e.g. to patients that have reduced numbers of stem cells and/or the ability to produce certain differentiated cell types, due to, for example, age, disease (e.g. cancers or autoimmune disease), congenital factors, environmental influences or contaminants and/or administered chemicals. In particular stem cells may be harvested from a patient prior to chemotherapy or radiotherapy and maintained and/or expanded and returned to that patient after chemotherapy or radiotherapy.

As an alternative example the stem cells may be used to provide cells from which a particular differentiated cell may be formed, e.g. neuronal cells, particularly in adult recipients where such suitable stem cells are absent or only low levels are present. The recipient of the stem cells is preferably also the donor, but may also be a different individual. The peptides of the invention may therefore be used to protect explanted tissue that contains stem cells (e.g. bone marrow cells) during culture in vitro or ex vivo.

Cells may also be maintained ex vivo or in vivo, for example to maintain viability during treatment that might normally affect their viability, e.g. during chemo- or radiotherapy. Agents as described herein, e.g. peptides of the invention can be used to reduce the susceptibility of stem cells to damage by such treatments by temporarily stopping or slowing the cell cycle of the stem cells. For example, peptides of the invention may be used to reduce the side effects caused by other cancer treatments, e.g. cytotoxic shock associated with many chemotherapeutic regimes. The cytoprotective effect of peptides of the invention on stem cells in vivo may also allow higher levels or doses of such cancer treatments to be used due to the decreased side-effects produced. For example, a higher dose of chemo-or radio-therapy may be possible.

Thus in a further aspect, the present invention provides a method of maintaining or expanding stem cells, wherein said method comprises at least the step of contacting said cells with an agent as described hereinbefore, preferably an antagonist, especially preferably an antagonist of the interaction between HOX and PBX, e.g. a peptide as described hereinbefore. This method may be used to maintain pluri- or toti-potency of the stem cells.

Preferably this method is performed in vitro or ex vivo, in culture, in which case the method may contain an initial step of harvesting stem cells from a donor. However, the method may also be used in vivo to maintain or improve the numbers of stem cells in an individual, particularly during exposure to agents or treatments that might cause stem cell damage. In such circumstances, the present invention provides a method of maintaining or expanding stems cells in a patient wherein said patient is administered an agent as described hereinbefore, preferably an antagonist, especially preferably an antagonist of the interaction between HOX and PBX, e.g. a peptide as described hereinbefore.

"Maintaining" the cells refers to maintaining the viability of a large proportion of the starting, e.g. harvested, cells with minimal cell division, during the course of the treatment or culture period.

"Expanding" the cells refers to at least some cell division, preferably significant cell division, to increase the numbers of cells during the course of treatment, or culture.

As referred to herein "culture" refers to the growth or maintenance of the cells in a controlled artificial environment, i.e. ex vivo. Standard techniques for culture of cells are well known. Preferably cells are cultured at 37° C., 5% $CO_2$ in a humidified atmosphere in a standard culture medium. Preferably said culture is conducted for at least 2 hours, preferably more than 24 hours; e.g. between 24 hours and 8 weeks.

"Contacting" as used herein refers to any suitable technique which allows the agent to have access, and thus the possibility of binding, to cells in the sample, e.g. by application to the culture medium.

After the cells have been maintained or expanded, the agent may be removed to recover pluri- or toti-potency. When the method is performed in vivo this may be achieved by ceasing administration and allowing the body to clear the agent. In vitro or ex vivo, the agent is removed from the culture medium, e.g. by washing and replacement with fresh medium. Alternatively, the agent may be removed by allowing it to degrade naturally.

Thus the invention provides a method of maintaining or expanding stem cells and or obtaining pluri- or toti-potent stem cells, in culture, preferably an expanded population of said cells, wherein said method comprises at least the steps of:

a) contacting said cells in culture with an agent which reduces or prevents PBX-dependent transcription regulation as described hereinbefore, preferably an antagonist, especially preferably an antagonist of the interaction between HOX and PBX, e.g. a peptide as described hereinbefore;

b) culturing said cells in the absence of said agent. It should be noted that the peptide becomes degraded within a few days during culture and thus active peptide is depleted. Thus, step b) may be performed without any prior washing if sufficient time has lapsed for degradation to occur. As mentioned previously, appropriate culture times are at least 2 hours, preferably more than 24 hours, e.g. between 24 hours and 8 weeks.

The method may contain an initial step of harvesting stem cells from a donor. Cells obtained by this and other methods of the invention comprise further aspects of the invention as does their use as a medicament.

The cells thus prepared by the above described in vitro or ex vivo methods may then be administered to an individual in need of such stem cells. Optionally. the cells may be modified prior to transplant, e.g. during the course of culturing or just prior to transplanting, e.g. by genetic modification, e.g. for gene transfer or to import a function not previously present in said cells, e.g. to compensate for a genetic deficit, e.g. by providing a missing factor, e.g. adenosine deaminase (ADA).

Thus in a yet further aspect, the present invention provides a method of treating an individual in need of stem cells wherein stem cells prepared according to the above described method are administered to said individual.

Preferably said individual in need of said stem cells is an individual who has (or will have) lower than normal or desirable levels of such cells, which condition may exist normally, e.g. through age or as a result of external factors e.g. through chemotherapy or radiotherapy. Especially preferably, said stem cells are derived from the recipient individual.

Thus in a preferred feature the present invention provides a method of improving the number of stem cells in a recipient individual wherein said method comprises at least the steps of:

a) harvesting stem cells from a donor, b) culturing said stem cells according to the methods described hereinbefore;

c) administering said cultured stem cells to said recipient individual.

Preferably said method is a method of improving the number of stem cells in a patient subject to chemotherapy or radiotherapy, wherein said method comprises at least the steps of:

a) harvesting stem cells from said patient prior to chemotherapy or radiotherapy, b) culturing said stem cells according to the methods described hereinbefore;

c) administering said cultured stem cells to said patient after completion of chemotherapy or radiotherapy.

Alternatively described, harvesting step a) in the methods above may be absent and step b) may comprise culturing stem cells harvested from the donor according to the methods described hereinbefore. Said cells may be harvested by obtaining a sample of cells, tissue or body fluid from said donor and optionally extracting the cells therefrom.

As used herein a "sample" refers to any material obtained from the donor, e.g. human or non-human animal, including embryonic, foetal, immature and adult stages of said animal, which contains stem cells and includes, tissues and body fluids. "Body fluids" include blood and spinal fluid. "Tissue samples" include tissue obtained by surgical interventions (e.g. bone marrow or liver) or by other means e.g. placenta and umbilical cord. The animals from which cells are derived or to which the methods are applied are preferably as described hereinbefore in connection with the methods of reducing aberrant cell division.

As used herein reference to "improving the number of stem cells" refers to increasing the number of stem cells to be added (preferably of the particular type to be added, e.g. haematopoietic stem cells) relative to the number present in the individual at the time at which administration would occur. Thus in the case of a patient subject to chemotherapy or radiotherapy the observed improvement is in the number of stem cells in a patient post-chemotherapy or post-radiotherapy. An improvement may also consist of the addition of certain stem cells previously absent or present in very low numbers, e.g. neuronal stem cells.

Alternatively expressed, the present invention provides the use of an agent (preferably an antagonist as described hereinbefore) in the preparation of a medicament for the treatment or prevention of conditions or disorders typified by a need for stem cells, preferably in treating or preventing conditions or disorders in which stem cell numbers are lower than normal, e.g. due to chemotherapy or radiotherapy, or in conditions in which the provision of stem cells may allow the production of one or more particular differentiated cells that are absent or present in abnormally low numbers, or lower numbers than desired, at the site of interest.

Conditions or disorders in which stem cell numbers are lower than normal include autoimmune disorders, radiotherapy, chemotherapy and certain viral infections. Conditions in which the use of stem cells by transplantation may provide appropriate differentiated cells which are absent or present at lower than normal or lower than desired levels include Alzheimer's disease, Parkinson's disease and other age-related disorders or conditions (including cosmetic treatments), multiple sclerosis, spinal cord injury, diabetes, chronic heart disease, end-stage kidney disease, liver failure and in which stem cells are used to replace destroyed or dysfunctional cells. Prevention of such conditions or disorders may be achieved by maintaining stem cells in a protected state by the use of agents as described hereinbefore.

The present invention further provides the use of cells prepared by the methods described hereinbefore in the preparation of a medicament for the treatment of conditions or disorders typified by a need for stem cells, as described above.

It should be noted that due to the effects of the aforementioned agents on aberrant cell division, even samples of stem cells containing such aberrant cells may be used and a dual effect of reducing the aberrant division while expanding the stem cells may be achieved. Thus the aforementioned agents may be used in vitro, ex vivo or in vivo to protect normal stem/progenitor cells whilst eliminating cells undergoing aberrant cell growth. This is particularly applicable to haematopoietic cells, e.g. when treating leukaemia/lymphoma.

Thus in a further preferred aspect the present invention provides a method of treating or preventing a condition or disorder in which aberrant cell division occurs. e.g. cancer, in a human or non-human animal, wherein said method comprises administering an agent, preferably an antagonist as described hereinbefore, wherein said agent is capable of both reducing said aberrant cell division and maintaining or expanding stem cells of said animal.

As described above, agents which reduce or prevent PBX-dependent transcription regulation, particularly HOX:PBX antagonists and particularly peptides as described hereinbefore have various clinical applications and thus a further aspect of the invention provides pharmaceutical compositions containing such agents. The use of these agents as a medicament forms a further aspect of the invention.

Thus, in a further aspect the present invention provides a pharmaceutical composition comprising an agent which reduces or prevents PBX-dependent transcription regulation as described hereinbefore preferably an antagonist, especially preferably an antagonist of the interaction between HOX and PBX, e.g. a peptide as described herein, or a polynucleotide or vector capable of expressing such a peptide, and a pharmaceutically acceptable excipient, diluent or carrier.

Pharmaceutical compositions as described herein for use as a medicament, preferably for use in treating or preventing disorders or conditions typified by aberrant cell division, or disorders or conditions typified by a need for stem cells, such as the conditions described herein, and methods of treatment or prophylaxis using such compositions and use of said agents for the preparation of a medicament for treating or preventing such disorders or conditions, form further aspects of the invention.

"Pharmaceutically acceptable" as referred to herein refers to ingredients that are compatible with other ingredients of the compositions as well as physiologically acceptable to the recipient.

Pharmaceutical compositions according to the invention may be formulated in conventional manner using readily available ingredients. Thus, the active ingredient (e.g. the peptide) may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, sterile packaged powders, and the like.

Compositions may additionally comprise molecules which assist or augment the action of the agents, preferably the peptides, described hereinbefore, e.g. cytotoxic agents such as antimetabolites, alkylating agents, cytotoxic antibiotics, topoisomerase I and/or II inhibitors, vinca alkaloids and monoclonal antibodies.

If required, the compositions may also contain targeting moieties attached to the active ingredient, e.g. a ligand which binds specifically and selectively to an endogenous receptor to allow targeting to a particular cell type or location, such as targeting to lymphocytes, monocytes, macrophages, endothelial cells, epithelial cells, blood cells, erythrocytes, platelets, eosinophils, neutrophils, natural killer cells, dendritic cells, brain cells, heart cells, lung cells, islet cells, kidney cells, cancer cells, hormonal gland cells, skin, bone, joints, bone marrow, gastric mucosa, lymph nodes, peyers patches, the omentum and other appropriate tissues.

Examples of suitable carriers, excipients, and diluents are lactose, dextrose, sucrose, sorbitol, mannitol, starches, gum acacia; calcium phosphate, aglinates, tragacanth, gelatin, calcium silicate, microcrystalline cellulose, polyvinylpyrrolidone, cellulose, water syrup, water, water/ethanol, water/glycol, water/polyethylene glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like. The compositions of the invention may be formulated so as to provide quick, sustained or delayed release of the active ingredient after administration to the patient by employing procedures well known in the art.

The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

Compositions may be in an appropriate dosage form, for example as an emulsion or in liposomes, niosomes, microspheres, nanoparticles or the like.

Administration of agents or compositions of the invention may take place by any of the conventional routes, e.g. orally, rectally or parenterally, such as by intramuscular, subcutaneous, intraperitoneal or intravenous injection, infusion, inhalation or topical administration, both to internal or external body surfaces etc. depending on the condition or disorder to be treated or prevented, optionally at intervals, e.g. 3 or more applications at 3~5 day intervals. Conveniently intravenous injection is used.

The active ingredient in composition of the invention may comprise from about. 0.01% to about 99% by weight of the formulation, preferably from about 0.1 to about 50%, for example 10%. The compositions are preferably formulated in a unit dosage form, e.g. with each dosage containing from about. 0.01 mg to about 1 g of the active ingredient, e.g. 0.05 mg to 0.5 g, for a human, e.g. 1-100 mg.

The precise dosage of the active compound to be administered and the length of the course of treatment will, of course, depend on a number of factors including for example., the age and weight of the patient, the agent to be used, the purpose of the treatment, the specific condition requiring treatment or prevention and its severity, and the route of administration.

Generally however, an effective dose may lie in the range of from about 1 µg/kg to about 10 mg/kg, e.g. from about 1 mg to 0.2 g of the agent per day, depending on the animal to be treated and the dosage form, taken as a single dose. Thus for example, an appropriate daily dose for an adult may be from 0.5 mg to 0.5 g per day, e.g. 1 to 100 mg of the polypeptide per day. In smaller animals the concentration range may be different and can be adjusted accordingly.

For in vitro or ex vivo use a concentration range of 1 µg/ml to 10 mg/ml for the agent, e.g. the peptide as described hereinbefore, is suitable.

Peptides of the invention may be used to assist or augment the action of agents used for conventional treatments, e.g. cytotoxic agents, to reduce their side effects, e.g. by protection of stem cells during treatment.

In one embodiment, a peptide of the invention is administered alongside one or more other therapeutically active agents. For example, a peptide of the invention may be used as a combinatorial chemotherapeutic agent. As shown in the Examples, peptides of the invention can induce some cancer cells, e.g. AML cells, to enter the cell cycle. Cells which have been stimulated in this way may therefore become more susceptible to conventional anti-cancer drugs. The peptides of the invention may therefore be used in combination with other anti-cancer agents, such as cytotoxic drugs, to target cancers such as leukaemia, more preferably acute myeloid leukaemia (AML) as explained above.

Peptides of the invention may also be used in combination with other anticancer therapies in order to protect the endogenous stem cell population. The inventors have discovered that the peptides of the invention are able to maintain normal stem/progenitor cells in a G0/G1 quiescent state. This cytoprotective ability may thus protect such stem cells from the effects of any anti-cancer treatment. This may be of particular use where the peptides of the invention are used in combination with cytotoxic agents which target dividing cells. By maintaining the normal stem cells of the patient in a quiescent state during such treatment, the side effects of the anti-cancer treatment on the endogenous stem cell population can be minimised. This reduction in the potential side effects may also allow a higher dose or level of the conventional treatment to be used on the patient than would otherwise be possible or safe.

Where a peptide of the invention is to be used in combination with or alongside one or more other therapeutic agents, for example an anti-cancer agent such as a cytotoxic drug, the agents may be formulated for simultaneous, sequential or separate administration. The agents may be formulated together in a single pharmaceutical composition. The agents may be formulated separately and may then be administered together, at the same time or sequentially, or at separate times during a course of treatment.

The following Examples illustrate the invention:

EXAMPLE 1

Effect of HXP Peptide on Growth, Cell Cycle and Viability In Vitro

In this example HXP peptide, a peptide generated to mimic the conserved region on HOX proteins, specifically the hexapeptide region of HOXB-4, was used in in vitro assays to determine its effects on cell growth, cell cycle and cell death on a variety of normal and abnormal cell lines or primary cell cultures.

Methods

1. HXP Peptide

To design a reagent that can prevent the interaction between PBX and HOX proteins, the highly conserved HOX hexapeptide sequence WYPWMKKHH (SEQ ID NO: 6) which is known to mediate this process (Morgan et al., 2000) was linked to a second peptide ('penetratin') based on the *Drosophila* Antennapedia protein, previously shown to mediate efficient movement of proteins across cell membranes (Derossi et al., 1998). This peptide is referred to as HXP peptide or HXP4.

The HXP peptide has the following sequence: (N-terminal) WYPWMKKHHRQIKIWFQNRRMKWK (C-terminal) and was prepared by routine chemical synthesis.

2. Blood Stem Cells Culture 2.1. Umbilical Cord Blood Collection and Mononuclear Cell Isolation Umbilical Cord Blood (UCB) specimens were collected from full-term deliveries scheduled for elective caesarian sections following hospital ethical regulations.

Samples were diluted 1 in 4 in PBS supplemented with a citrate-based anti-coagulant (0.6% ACD-A, Baxter, France) and Bovine Serum Albumin (0.5% fraction V, Sigma Aldrich, UK) at pH=7.4 and referenced as "ACD-A buffer". Diluted UCB was carefully overlaid in a 1:4 ratio onto a research grade Ficoll-Paque solution (d:1.077 g/cm$^3$, Pharmacia Biotech, Sweden) prior to Centrifugation (400 g, 30 minutes, 22° C.). The mononuclear cells (MNC) layer was extracted, washed twice in ACD-A Buffer, pelleted (400 g, 10 minutes) before resuspending in ACD-A buffer and cell aliquots taken for cell viability/enumeration using trypan blue (Sigma Aldrich).

2.2. AC133+ Cell Immunomagnetic Selection

AC133+ cells were obtained from MNC after immunomagnetic separation using the AC133 mini-MACS selection kit (Miltenyi Biotec, Germany): labelling volume 500 μl/10$^8$ cells in ACD-A buffer containing Fc Receptor-blocking reagent (100 μl, 5 min incubation, 4° C.) before adding colloidal super-paramagnetic MACS MicroBeads conjugated to monoclonal mouse anti-human AC133/1 antibody (100 μl IgG1 isotype, 25 min incubation, 4° C.). Cells were then washed (5 ml ACD-A buffer, 400 g, 10 min, 4° C.) before resuspended cells in 500 μl ACD-A buffer were applied to a chilled MACS positive selection column (MS+/RS+) on a magnet. The column was rinsed with cool ACD-A buffer (4×500 μl) and the AC133− cell population retained at 4° C. After magnet removal AC133+ cells were eluted with 1 ml of cold ACD-A buffer. The AC133+ cell fraction was reapplied to a new column, prior to cell enumeration and viability assays.

2.3. Short-term Ex-Vivo AC133+ Cell Expansion Cultures with HXP Peptide

AC133+ cells were seeded in duplicate in liquid culture system at 2-4×10$^4$ cells/ml. The liquid culture system consisted (in 1.5 ml total) of Iscove Modified Dulbecco's Medium (Life Technologies, UK) supplemented with Foetal Calf Serum (10%, Sigma Aldrich) and gentamycin (50 μg/ml Life Technologies). Culture systems were supplemented with growth factors 'TPOFLK' (Thrombopoietin 10 ng/ml, Flt-3 Ligand 50 ng/ml) and HXP peptide (20 μg/ml). AC133+ cells were also cultured with TPOFLK and the control peptide (WAPWEDDHHRQIKIWFQNRRMKWKK (SEQ ID NO: 25), same concentration as HXP). Every 7 days, the medium was changed and when required: (i) HXP peptide was added (concentration maintained) or (ii) withdrawn, (iii) Hox B4 protein (20 μg/ml, recombinant full length *Xenopus laevis* sequence) was added. Cells were cultured for up to 18 days at 37° C., 5% $CO_2$ in humidified atmosphere. Cultured cells were then counted at various time points using trypan blue exclusion method described above.

3. Leukaemic Cell Lines Culture

KG1a, KG1, HL60 and U937 cell lines were obtained from the ATCC (catalogue Nos. CCL-246.1, CCL-246, CCL-240 and CRL-1593.2, respectively.

U937 contains the chromosomal rearrangement of the HRX gene situated at 11q23 translocation, one of the most frequent genetic changes in childhood leukaemias of both myeloid and lymphoid lineage and in treatment induced secondary leukaemias (Butler et al., 1997). KG1a is derived from KG1 cells and is considered to be very undifferentiated because, like primitive myeloid progenitors, they display a CD34 high CD38 negative phenotype (Koeffler et al., 1980). KG1a and HL60 are able to differentiate into granulocyte or monocyte cells depending on the stimulus (Koeffler and Golde, 1978, Sundstrom and Nilsson, 1976);

Cell lines were seeded at 1-5×10$^5$ cells/ml in liquid culture system made of RPMI-1640 medium (Life Technologies, UK) supplemented with Foetal Calf Serum (10% Sigma Aldrich) and gentamycin (50 μg/ml, Life Technologies) and at least in duplicate. When required the HXP peptide was added to the medium (20 μg/ml). Cell lines were cultured for up to 7 days at 37° C., 5% $CO_2$ in humidified atmosphere. Cultured cells were then counted at various time points using trypan blue exclusion method described above.

4. Cell Cycle Analysis

Cells to be investigated were harvested and washed in PBS at 400 g for 10 min. Pelleted cells were then fixed in ice-cold 70% ethanol. Fixed cells were subsequently washed twice in PBS (600 g; 10 min) and incubated in 100 μl of ribonuclease (100 μg/ml; Sigma Aldrich) for 5 min (room temperature) prior to addition of 400 μl of propidium iodide (50 μg/ml; Sigma Aldrich) and 30 minutes incubation (37° C.). Cells were then analysed for cell cycle status on FACScan flow cytometer (Becton Dickinson, USA) and using WinMDI and Cylchred softwares.

5. RT-PCR

Total RNA was extracted from cultured human cells using the Rneasy mini kit (Quiagen) and following the manufacturer's instructions. 3 μg of RNA was used in subsequent reverse transcription reactions. The RNA was mixed with a poly $T_{15}$ oligo to 5 microgrammes/ml and heated to 75° C. for 5 minutes. After cooling on ice, the following additional reagents were added: dNTPs to 0.4 mM, RNase OUT (Promega) to 1.6 U/μl, Moloney Murine Leukemia Virus Reverse Transcriptase (M-MLRvT) RnaseH— point mutant (Promega) to 8 U/μl and the appropriate buffer (supplied by the manufacturer) to x1 concentration. The mixture was incubated for one hour at 37° C., heated to 70° C. for two minutes and cooled on ice.

PCR reactions were all performed in a total volume of 40 μl. For each we used 1 μl of the M-MLRvT reaction (as described above), 0.2 nmols of each primer and 20 microliters of Redimix pre-mixed PCR components (Sigma). All reactions were cycled at 94° C. for 30 seconds, 55° C. for 30 seconds and 72° C. for 60 seconds. 30 cycles were used for all primer sets except those for beta-actin, for which 23 cycles were used.

Primer Sequences for RT-PCR

AC133(U): 5' CAG TCT GAC CAG CGT GAA AA 3

AC133(D): 5' GGC CAT CCA AAT CTG TCC TA 3

Beta-actin(U): 5' ATG TAC CCT GGC ATT GCC GAC 3'

Beat-actin(D): 5" GAC TCG TCA TAC TCC TGC TTG 3'

CD34(U): 5' TGA AGC CTA GCC TGT CAC CT 3'

CD34(D): 5' CGC ACA GCT GGA GGT CTT AT 3'

CD38(U): 5' GGG TGA TAC ATG GTG GAA GAG 3'

CD38(D): 5' TGT GCA AGA TGA ATC CTC AGG 3'

HOXA9(U): 5' AAT AAC CCA GCA GCC AAC TG 3

HOXA9(D): 5' ATT TTC ATC CTG CGG TTC TG 3

HOXB4(U): 5' AGC GAT TAC CTA CCC AGC GAC 3'

HOXB4(D): 5' AGG GTC CCG GCA GGC CGC 3'

HOXB8(U): 5' TGG AGC TGG AGA AGG AGT TC 3'

HOXB8(D): 5' CGC TCC AGC TTC TGT TTC TC 3'

Results

Figure 3:
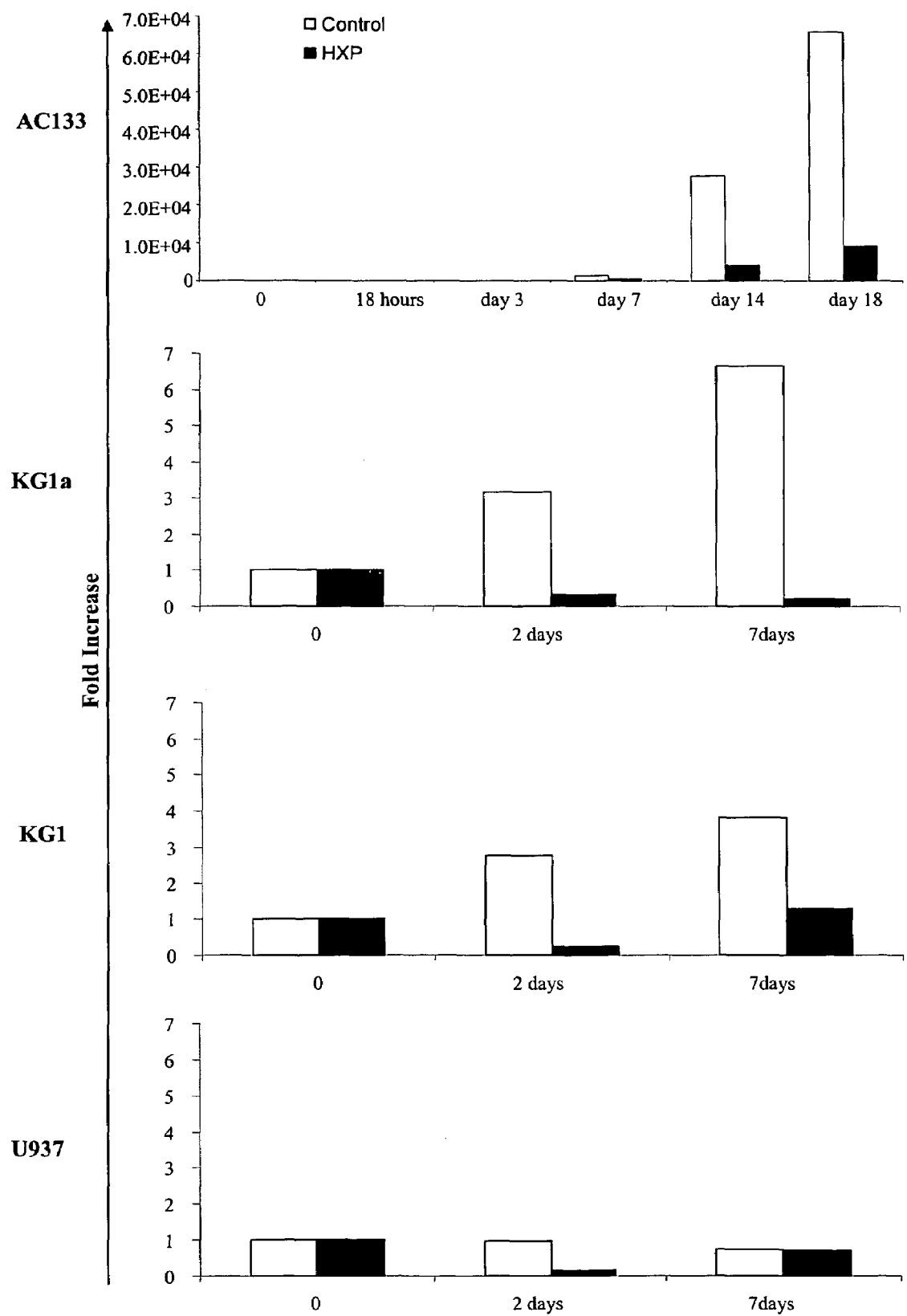
FIG. 3 is similar to FIG. 1 and shows the longer term effects of HXP peptide on the cell growth of AC133+ KG1a, KG1 and U937 cells.

The results of the above described experiments are shown in FIGS. 1 to 5. FIG. 1 shows the effect of HXP peptide on the cell growth of various cells and shows that the peptide protects immature blood stem cells (AC133+ cells) by maintaining them in a quiescent state and slowing their growth. HXP inhibits the leukaemic cell lines (KG1a, KG1, HL60 and U937) rapidly (between 2 and 6 hours), but the inhibition also appeared over longer time periods (FIG. 3). (Whilst leukaemic cell lines can spontaneously proliferate in liquid culture systems, AC133+ cells are primary haematopoietic stem/progenitor cells from umbilical cord blood. AC133+ cells were therefore cultured with optimized cytokine cocktail necessary for their expansion which is reflected in their greater increase in proliferation relative to the leukaemic cell lines.) It appears that immature leukaemic cells such as KG1 and KG1a may be propelled into the cell cycle by the HXP peptide (FIG. 2), whereas the cell cycle of more mature leukaemic cells (HL60 and U937) is slowed.

Figure 4:
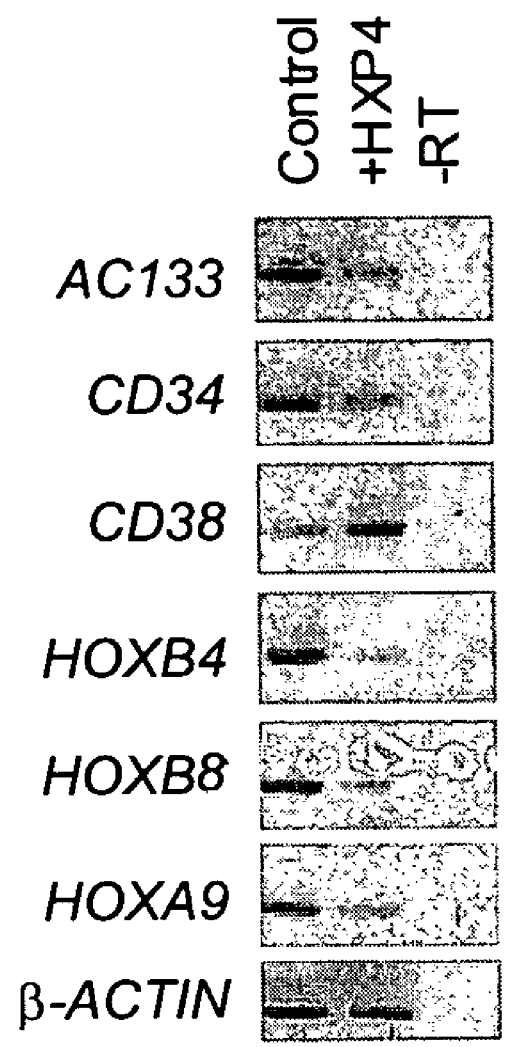
FIG. 4 shows the results of RT-PCR to detect various markers of stem/progenitor cells, or markers of maturation/differentiation in KG1a cells after 7 days of treatment with HXP peptide.
Figure 5:
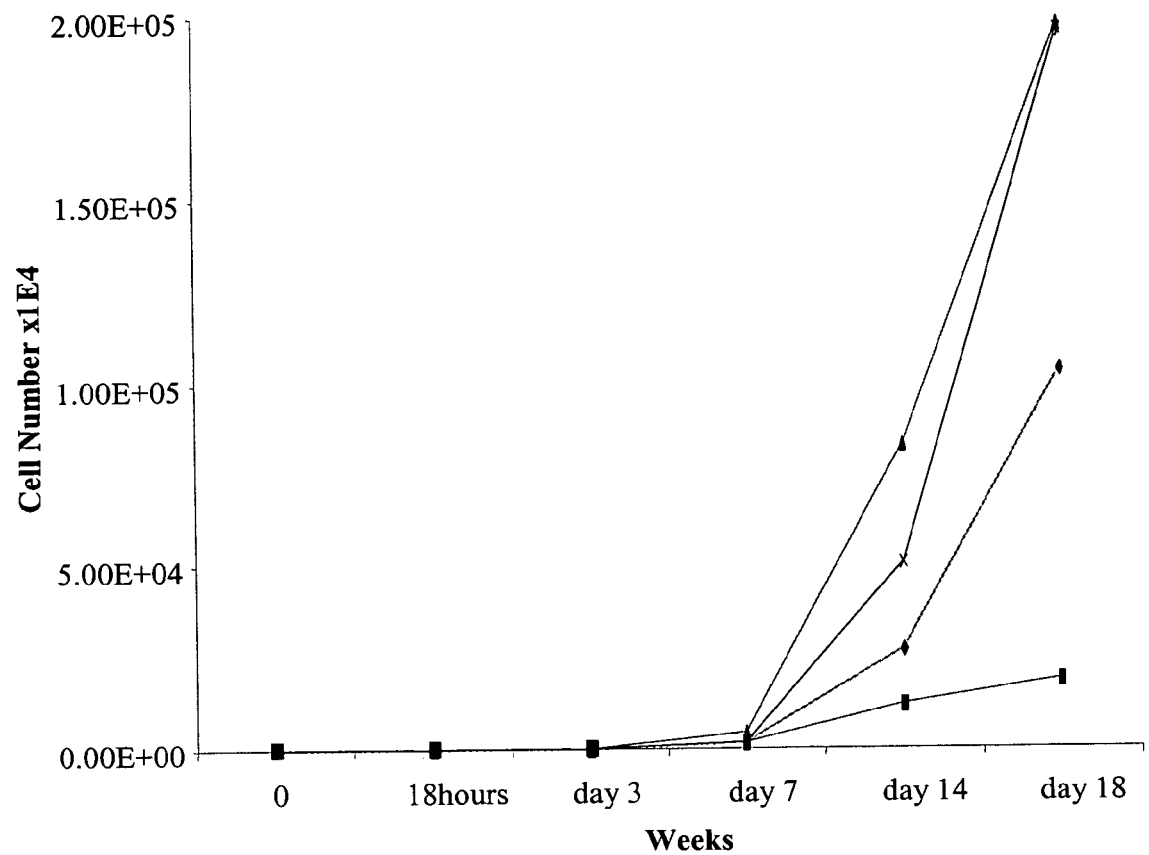
FIG. 5 shows the effect of HXP peptide on the cell growth of AC133+ cells in which -▲- is the control with no HXP added, -■- shows cells to which HXP was added at days 0, 7 and 14, -♦- shows cells to which HXP peptide was added at day 0, but withdrawn at days 7 and 14, and -X- shows cells to which HXP peptide was added at day 0 and on day 7 HXP peptide was withdrawn and HOX B4 protein added.

Markers of stem/progenitor cells (AC133, CD34, HOXB4, HOXB8 and HOXA9) were diminished in KG1a cells treated with HXP peptide for 7 days, whereas markers of maturation/differentiation (CD38) were elevated (FIG. 4).

The effect of HXP peptide in maintaining stem cells in a quiescent state was found to be reversible. It will be noted from Example 5 that withdrawal of the HXP peptide led to a resumption in growth of AC133+ cells (FIG. 5) and a return of markers of stem cells/progenitors.

HXP peptide slowed AC133+ proliferation and this coincided with up-regulation of CD38 gene expression, whilst HOX B4, B8 and A9 genes were down-regulated from as early as day 3. On withdrawal. of HXP peptide at 7 days, AC133+ cells started to proliferate again, and reverted to near control levels when co-stimulated with HOX B4. This increase in proliferation correlated with progressive CD38 gene expression down-regulation and up-regulation of HOX B4, B8 and A9 genes.

EXAMPLE 2

Cross-Reactivity of HXP Peptide with All PBX Proteins

Methods

HXP and control peptides were as described in Example 1. KG1a cells were grown as described in Example 1. KG1a cells were cultured for 24 hours without treatment, or in the presence of 1 μM HXP peptide or control peptide. The cells were harvested and lysed. One aliquot of the cells was subject to cross-linking. Frozen cells were lysed using standard techniques and 100JLl of lysate was incubated for 30 minutes at room temperature in 4 mM 1-ethyl-3-[3-(dimethyl-amino) propyl]carbodiimide (EDC), 4 mM sulpho-NHS, 20 mM HEPES (pH 7.5), 5 mM $MgCl_2$, and 0.03% (w/v) f3-DM to cross-link non-covalently associated proteins. The reaction was stopped by the addition of ammonium acetate to a final concentration of 50 mM. The other aliquot was frozen without cross-linking.

Proteins were extracted from the cells of both aliquots by standard techniques and separated by gel electrophoresis. The gels were probed by Western blot with an antibody raised against PBX1, 2 and 3 (sc-888, Santa Cruz Inc. USA) or an anti-beta actin antibody (sc-1615, Santa Cruz Inc. USA).

Results

Figure 6:
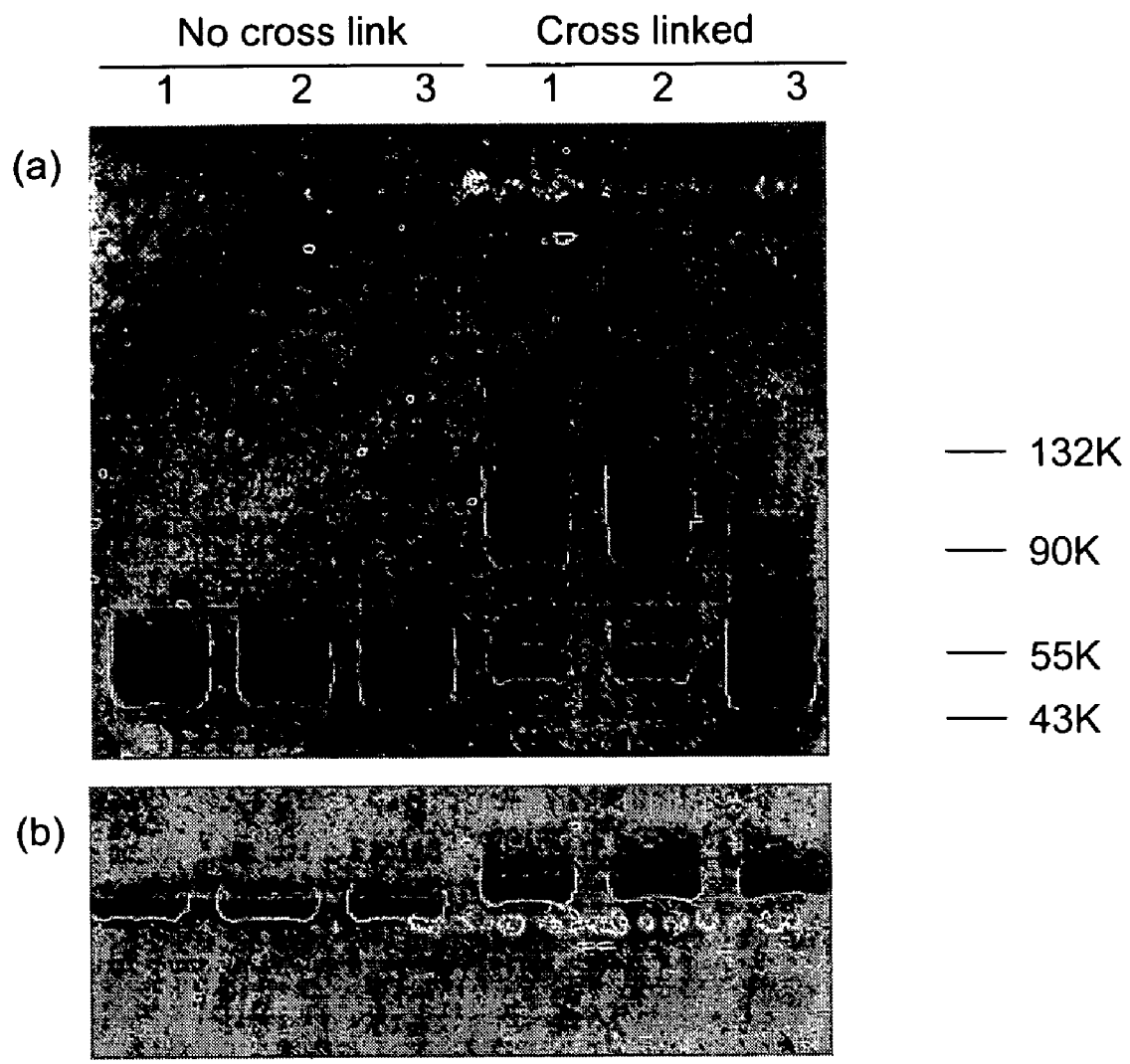
FIG. 6 shows the disruption of HOX and PBX binding by HXP peptide. Western blot of protein extracted from CD133+ cells and probed with (a) an antibody raised against PBX1, 2 and 3 isoforms and (b) an anti-beta actin antibody. 'Crosslinked'—protein was extracted in 1-ethyl-3-[3-(dimethylamino)propyl]carbodiimide (EDC) to cross link non-covalently associated proteins. 1—untreated cells; 2—CXP4 peptide-treated cells; 3—HXP peptide-treated cells. The presence of HXP peptide distrupted the formation of PBX/HOX dimers (90-125 kDa) from PBX monomers (52 kDa).

It will be noted from FIG. 6 that whilst the PBX proteins from untreated and control peptide treated cells were associated with other proteins (ie. HOX proteins), none of the PBX isoforms from the HXP peptide treated cells were associated with other proteins. This illustrates that the peptide of the invention has a global effect on all PBX proteins and thus prevents the interaction between all PBX and HOX proteins.

EXAMPLE 3

Methods

1. Cell Culture

CD133+ cells (another name for AC133+ cells) were seeded in duplicate at $4\times10^4$ cells/ml in IMDM (Life Technologies), 10% FCS (Sigma Aldrich) and gentamycin (50 μg/ml Life Technologies) and Thrombopoietin (TPO) 10 ng/ml, Flt3-Ligand (FL) 50 ng/ml & c-KitL (K) 20 ng/ml), all obtained from R and D systems Ltd., UK. (Forraz et al., 2002). The HXP peptide (N-term: WYPWM KKHHR QIKIW FQNRR MKWKK: C-term; Eurogentec, Belgium) and control CXP peptide (N-term: WCCLA DRHGR QIKIW FQNRR MKWKK: C-term; Eurogentec, Belgium) were added to culture medium at a concentration of 20 μg/ml. To withdraw peptides from culture, cells were washed twice in IMDM or RPMI and reseeded at prewash cell densities. Primary cells were cultured for 3 weeks at 37° C., 5% $CO_2$ in humidified atmosphere and enumerated by a tryptophan blue exclusion method with a heamocytometer.

KG1a, HL60 and U937 cell lines were seeded as described in Example 1.

All cell lines were grown with HXP peptide (20 μg/ml) or CXP (20 μg/ml). Cell lines were cultured for various time points at 37° C., 5% $CO_2$ in humidified atmosphere and enumerated at various time points.

2. Western Blotting of PBX and PBX/HOX Dimers

Protein was extracted from HXP-treated or CXP-treated CD133+ cells (20 μg/ml). C-20 antibody that recognises all three human PBX gene proteins (sc-888, Santa Cruz Biotechnology Inc., USA; Monica et al., 1991). Protein cross linking was performed with 2 mM 1-ethyl-3-[3-(dimethylamino)propyl]carbodiimide (EDC) (Pierce Biotechnology, USA), in cell lysates diluted 1:10 in conjugation buffer (0.1M 2-[N-morpholino]ethane sulphonic acid, pH 5). After 15 minutes at room temperature the reaction was stopped by adding 2-mercaptoethanol to 20 mM and excess reagents were removed using a D-Salt Dextran desalting column (Pierce, USA).

3. RT-PCR Analysis

Total RNA was isolated from liquid nitrogen snap-frozen cells using RNeasy Mini Kit protocol (Qiagen, Crawley, UK). 50 μl reverse transcription reactions using 1 μg of RNA per reaction heated at 75° C. cDNA with 1 μg of oligo-dT for 10 mins. Samples were cooled on ice and mixed with 200 units of M-MLV reverse transcriptase (Promega, Southampton, UK) in its associated buffer, 400 μM of dNTPs (Promega), and 40 units of RNAseout (Invitrogen, Paisley, UK). Samples were then incubated at 37° C. for one hour and finally heated at 75° C. for 5 mins. PCR reactions (35 cycles, 94° C. 30 sec, 55° C. 30 sec, 72° C. 1 min) were carried out in a 20 μl reaction using JumpStart ReadyMix REDTaq DNA polymerase (Sigma-Aldrich) using an identical amount of cDNA per reaction with 1 μM of forward and reverse primers.

Results

1. A Cell Permeating Peptide Mimic of the HOX Hexapeptide Sequence Prevents PBX from Binding to Other Proteins.

The ability of HXP peptide to prevent HOX/PBX interactions was tested by adding it to a CD133+ HSPC population in vitro. These cells are derived from umbilical cord blood, and are selected for their expression of the surface antigen CD133, a known marker of early HSPCs (Forraz et al., 2002).

CD133+ cell protein was analysed for the three different isoforms of PBX (Monica et al., 1991) by western blotting, with or without cross linking (FIG. 6). HXP peptide, but not the control peptide CXP, prevented binding of PBX to other proteins under these conditions.

2. HXP Peptide Induces Reversible Inhibition of CD133+ Cell Proliferation

Figure 7A:
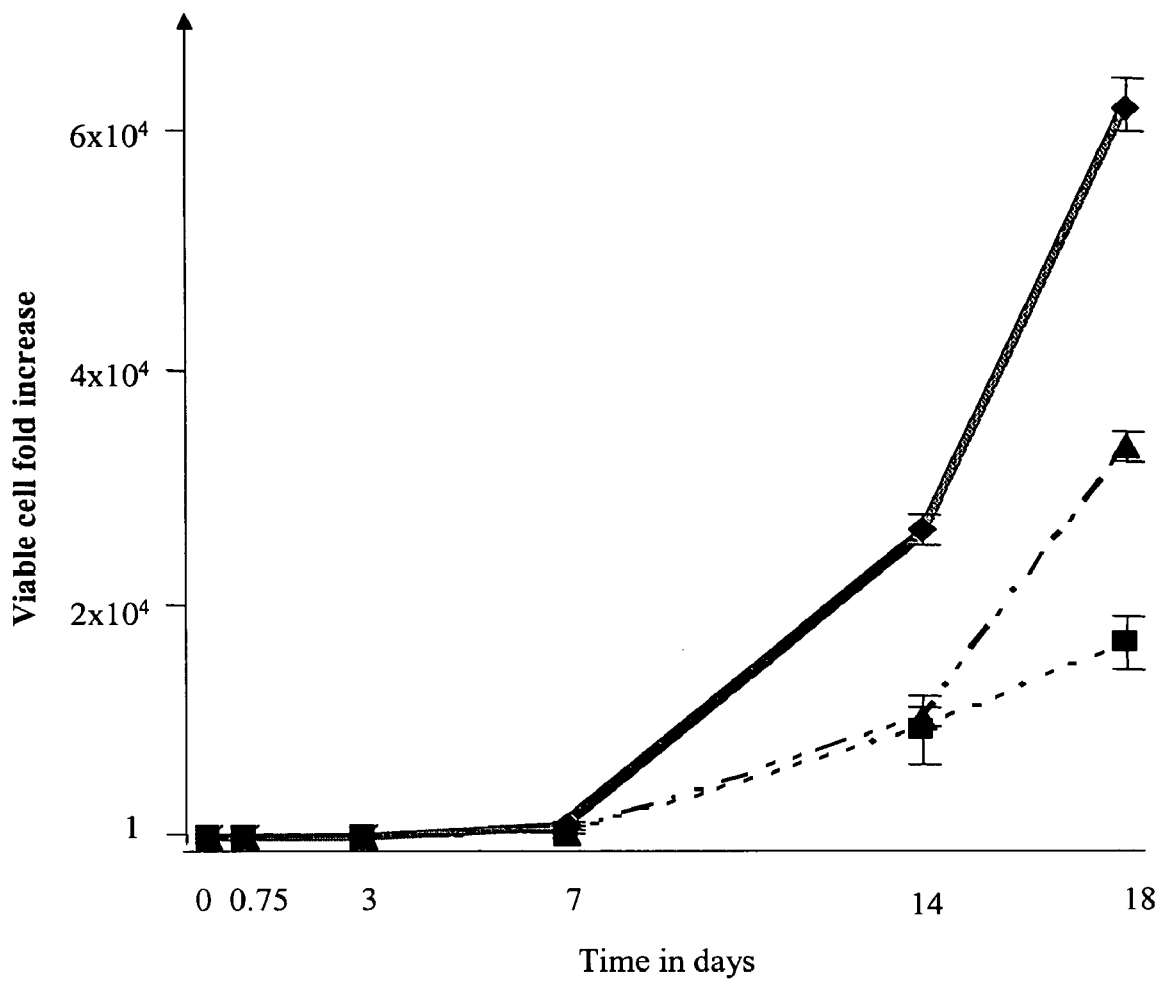
FIG. 7 shows HXP peptide treatment of CD133+ cells. Viability and cell number were monitored in culture over 18 days. (A) Mean viable cell fold increase (±S.E.M.) over 18 days of cells treated with HXP peptide or CXP4. Diamonds—addition of CXP4 peptide at day 0; 7 and 14; squares—addition of HXP peptide peptide at day 0; 7 and 14; triangles—addition of HXP peptide at day 0 and withdrawal at day 7. (B) Expression of a range of PBX/HOX target genes analysed by RT-PCR at day 18. (1) untreated, freshly isolated CD133+ cells. (2) CXP4 treated cells. (3) addition of HXP peptide peptide at day 0; 7 and 14. (4) addition of HXP peptide at day 0 and withdrawal at day 7. Transcripts not detected in 18 day HXP peptide treated cells were restored by removal of HXP peptide on day 7. Beta actin expression is included as a loading control. Lanes were run in duplicate. -, no expression detected; +, expression detected; ++, expression at least five fold higher than in (+). Data representative of three experiments.

CD133+ cells were grown in cytokine supplemented liquid cultures for 18 days with either HXP peptide or CXP peptide (FIG. 7a) to determine the effect of HXP peptide on cell proliferation in early HSPC. Treatment of CD133+ cells with HXP peptide inhibited growth by an average of 3.7 fold at day 18 ($p<0.001$) when compared to the CXP peptide-treated cells. Withdrawal of the HXP peptide from cell culture at day 7 enabled a resumption of cell proliferation when compared to the 18 day-HXP peptide treated cell population ($p<0.01$), indicating that HXP peptide inhibition is reversible. The cellular morphology and integrity of these populations showed no apparent change in response to HXP peptide or CXP peptide addition (data not shown).

3. HXP Peptide Treatment of CD133+ Cells Induced Down-Regulation of Primitive HSPC Markers The expression of a number of genes associated with HSPC differentiation and cell cycle control were examined by RT-PCR of RNA extracted from cells with the growth profiles shown in FIG. 7a. After 18 days in thrombopoietin, Flt-3 ligand and c-kit ligand (TPOFLK) supplemented culture, control peptide-treated CD133+ cells maintained the expression of a series of genes associated with the non-differentiated HSPC phenotype including CD133, TERT (telomere reverse transcriptase), HOXB8, HOXA9, and HOXB4 (which is up-regulated by thrombopoietin itself (Kirito et al., 2003). The CD38 gene, linked with HSPC differentiation, was not expressed. HXP peptide treatment of CD133+ cells significantly down regulated a range of HOX-PBX target genes (FIG. 7b) involved in cell cycling (CDC25 (Donzelli and Draetta, 2003) and CDK2 (Siebert et al., 1996)), proliferation (N-Ras (Hall et al., 1993; Scheele et al., 2003), Ras-like GTP binding protein (Bos, 1997)), migration (matrix metalloproteinases -MMP19- and -MMP1- (Stamenkovic, 2003; Murphy et al., 1999)), growth factor mediated signal transduction (mitogen-activated protein kinase -MAPK- (Reddy et al., 2003) and RAB27A (Chen et al., 1997; Seabra et al., 2002)), apoptosis (Bcl-2 homologue -Bak2- and tumour suppresser -p53- (Vermeulen et al., 2003)), transcription (CCCTC-binding factor -CTCF- (Ohlsson et al., 2001), eukaryotic translation initiation factor 4E -EIF4E- (Thornton et al., 2003), and the primitive HSPC markers (CD133 (Forraz et al., 2002), CD34 (REF), TERT (Allsopp et al., 2003), HOX B4, B8 and A9). The CD38 gene was up-regulated. Withdrawing HXP peptide at day 7 resulted in the up-regulation of all of these genes with the exception of MAPK, and in the down-regulation of CD38.

Figure 8:
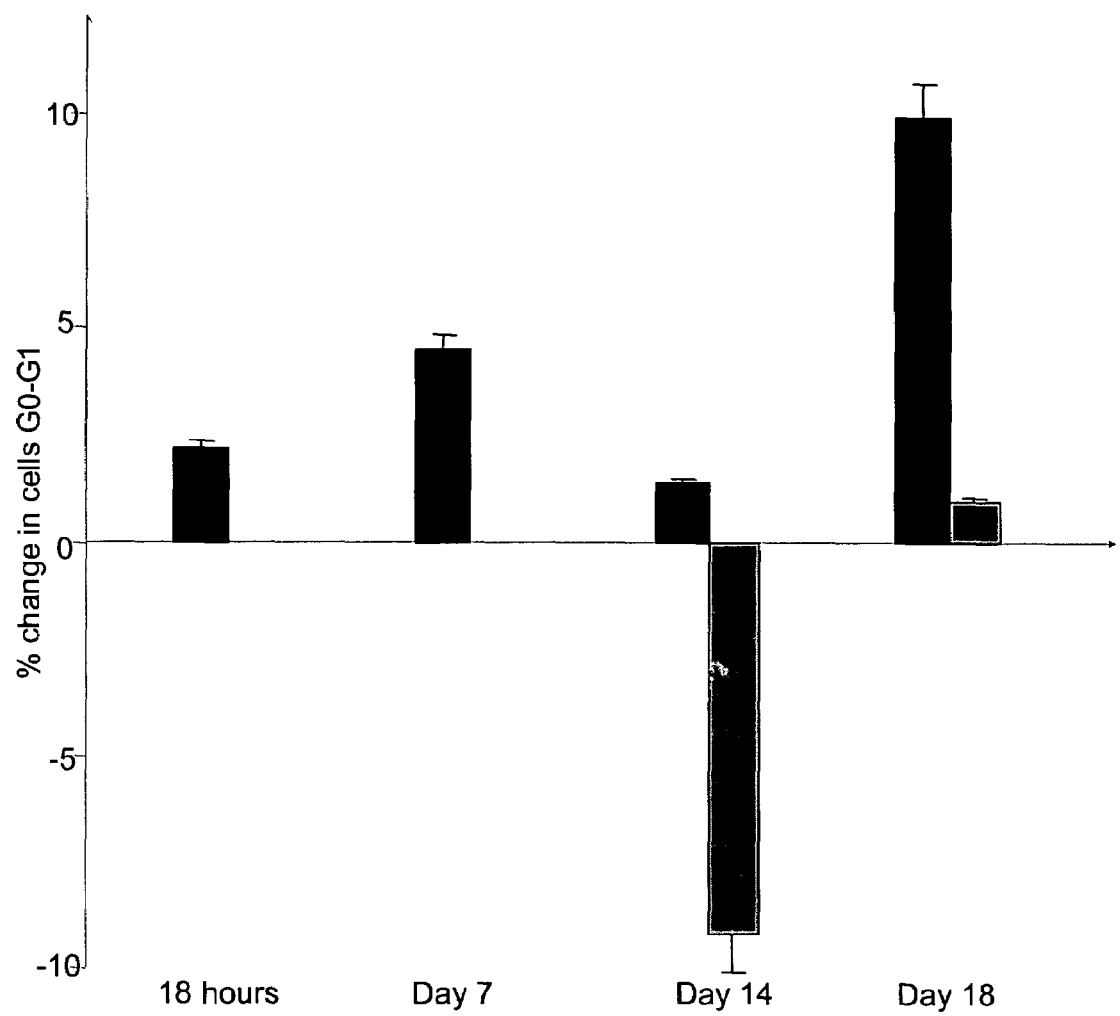
FIG. 8 shows the effect of HXP peptide on CD133+ cell cycling. Cultured CD133+ cells were analysed for the percentage of cells in G0-G1 phase of the cell cycle. HXP peptide treatment maintained a higher proportion of cells in G0-G1 phase of the cell cycle than compared to CXP4-treated cells. HXP peptide withdrawal allowed more CD133+ cells to enter the cell cycle. Results are expressed as percentage of change in comparison to CXP4 (control peptide) treated cells. Black bars—cells treated with HXP peptide at days 0, 7 and 14. Grey bars—cells treated with HXP peptide at day 0 only.

4. HXP Peptide Maintains Expanding CD133+ cells in Phase G0-G1 of the Cell Cycle The cell cycle status of CD133+ cells was analysed in TPOFLK supplemented cultures with and without HXP (FIG. 8). Consistent with an enriched stem cell population, 93% of cells were in G0-G1 at day 0. Over 18 days a higher proportion of HXP peptide-treated CD133+ cells were in G0-G1 phase of the cell cycle compared to CXP4 treated cells. This difference rose incrementally with HXP peptide-treated cells having 9.9% more cells in phase G0-G1 of the cell cycle than the control group at day 18 of culture ($p<0.05$) (FIG. 8). Upon withdrawing HXP peptide from liquid culture, a lower proportion of cells remained in phase G0-G1 of the cell cycle when compared to the HXP peptide-treated group.

5. HXP Peptide Inhibits the Growth of KG1a, HL60 and U937 Leukaemic Cell Lines

Figure 9A:
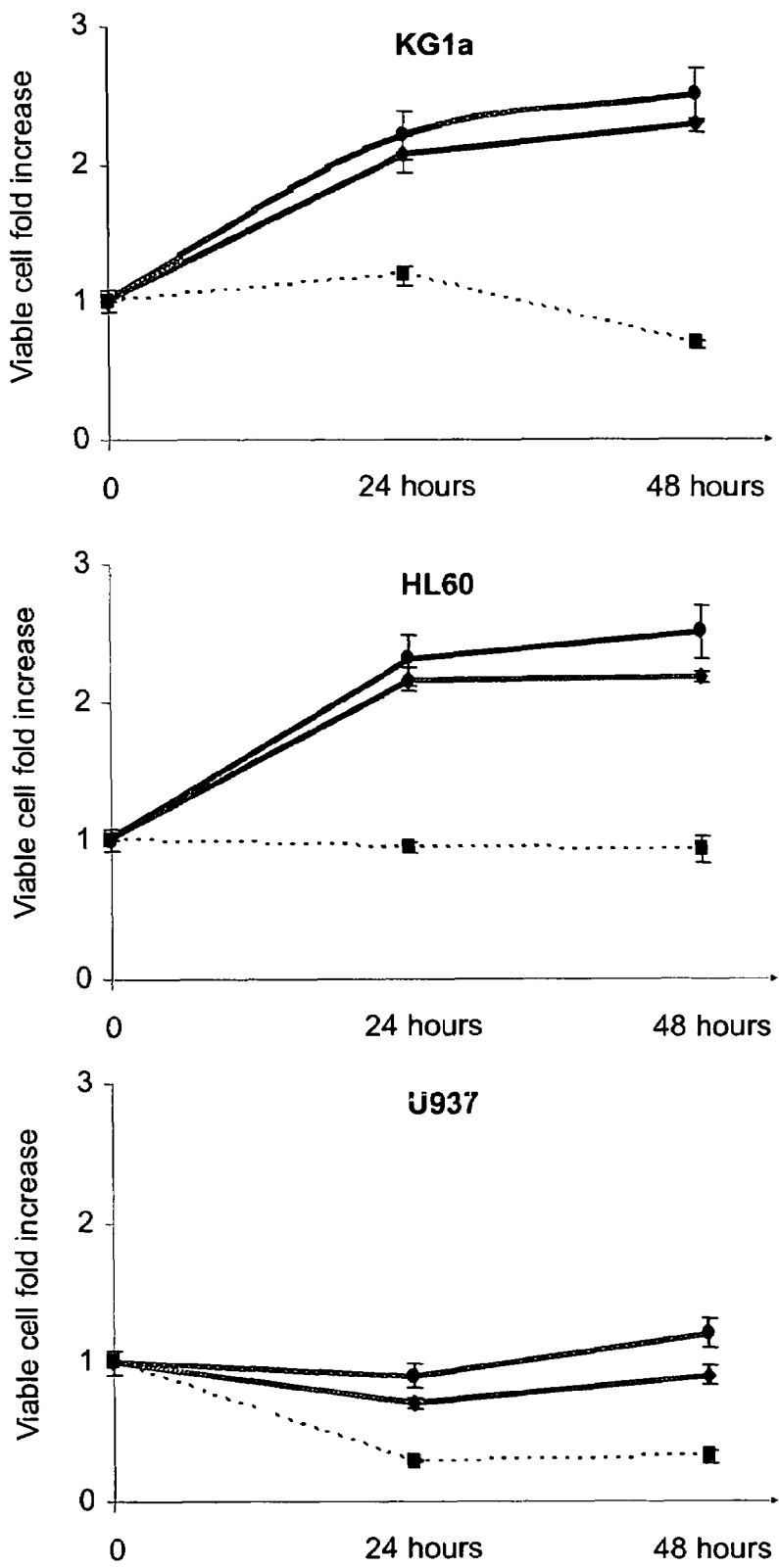
FIG. 9 shows the effects of HXP peptide treatment on leukaemic cell lines. The inhibition of CXP and HXP peptides was evaluated over 48 hours in culture. A). Comparison of cell number in the presence of HXP or control CXP4 peptide. Data representative of 4 experiments (=/-SEM). Circles—untreated cells; diamonds—CXP4 treated cells; squares—HXP peptide treated cells. B) Table showing the expression of PBX/HOX target genes analysed by RT-PCR of cells at day 18 of culture. Beta actin expression is included as a loading control. Lanes were run in duplicate. C, CXP4 treated; H, HXP peptide treated. -, no expression detected; +, expression detected; ++, expression at least five fold higher than in (+).

The role of HOX gene dysregulation in haematological malignancies was investigated by studying the growth of leukaemic cell lines KG1a (M0 French-American-British (FAB) classification), HL60 (M2/M3 FAB Classification (Collins et al., 1977)) and U937 a bi-phenotypic cell (myeloid histiocytosis (Sundstrom and Nilsson, 1976)). U937 contains the chromosomal rearrangement of the HRX gene situated at 11q23 translocation, one of the most frequent genetic changes in childhood leukaemias of both myeloid and lymphoid lineage and in treatment induced secondary leukaemias (Butler et al., 1997). KG1a is derived from KG1 cells and is considered to be very undifferentiated because, like primitive myeloid progenitors, they display a CD34 high CD38 negative phenotype (Koeffler et al., 1980). KG1a and HL60 are able to differentiate into granulocyte or monocyte cells depending on the stimulus (Koeffler and Golde, 1978, Sundstrom and Nilsson, 1976). HXP peptide exerted a potent cell growth inhibition on all three cell lines, apparent within two hours (FIG. 9a). The cellular morphology and integrity of these populations showed no apparent change in response to HXP peptide or CXP4 addition (data not shown).

6. HXP Peptide Treatment of KG1a, HL60 and U937 Leukaemic Cell Lines Influenced Expression of Several HOX-PBX Transcription Factors Target Genes.

The effect of HXP peptide on HOX/PBX target genes was examined in leukaemic cell lines (FIG. 9b). In the KG1a cell line, which is representative of relatively undifferentiated myeloid cells, HXP peptide treatment induced down-regulation of CD133, CD34, HOXB4, B8 and A9 gene expression and up-regulation of CD38. U937 and HL60 cell lines did not express CD133 or CD34. However, down-regulation of HOXB4 and A9 gene expression was observed upon HXP peptide treatment, whereas CD38 was up-regulated and HOXB8 gene expression was unchanged.

The N-RAS oncogene (Hall et al., 1983; Scheele et al., 2003) was completely down-regulated by HXP peptide treatment in all of the cell lines. HXP peptide treatment did not alter the expression of the other genes examined with the exception of; CDC25 (down-regulated in U937 cells (Donzelli and Draetta, 2003)), MMP1 (down-regulated in KG1a and U937 cells (Stamenkovic, 2003)), and MMP19 (down-regulated in KG1a (Murphy et al., 1999)) (FIG. 9b).

7. HXP Peptide Treatment of KG1a, HL60 and U937 Leukaemic Cell Lines Induces Cell Cycling Activity.

Figure 10:
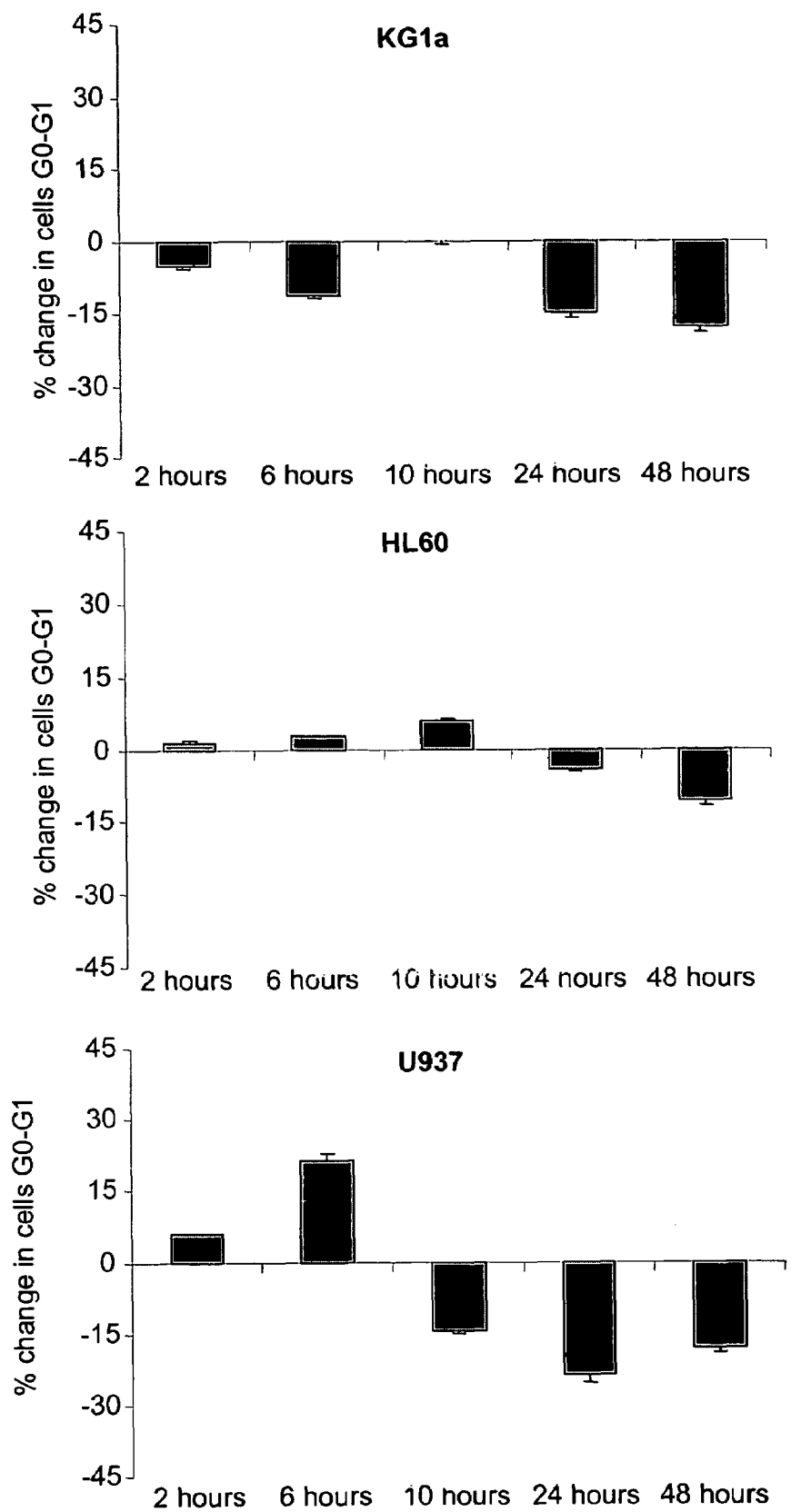
FIG. 10 shows the effects of HXP peptide on the cell cycle of leukaemic cell lines. The proportion of KG1a, HL60 and U937 cells in G0-G1 phase of the cell cycle upon HXP peptide treatment was compared to CXP4. Cells were synchronised in G0-G1 phase of the cell cycle by exposure to 0.5 mM L-mimosine. Results are expressed as the mean percentage of four experiments (+/-SE).

KG1a, HL60 and U937 cell cycle profiles were analysed over 48 hours in culture with HXP peptide or the control peptide (FIG. 10). The effect of HXP peptide on non-synchronised cells varied considerably (data not shown). Synchronising cells in G0-G1 by pre-conditioning them showed that HXP peptide induces a significantly higher proportion of cells to leave the phase G0-G1 and enter the cell cycle.

Discussion

The function of most HOX genes is dependant upon their interaction with the PBX co-factor via a conserved hexapeptide sequence (Chang et al., 1996; Piper et al., 1999; Passner et al., 1999). In this study the HOX/PBX interaction was blocked by HXP peptide, a mimic of the HOX hexapeptide fused to a delivery motif derived from the Antennapedia protein (Derossi et al., 1998).

CD133 expression on HSPC precedes CD34 expression (Bhatia et al 2001, McGuckin et al 2003b) and defines an early HSPC population with high proliferation and long term repopulation potential (de Wynter et al 1998, Pasino et al 2000). Treating this pluripotent HSPC populations with HXP peptide blocked their proliferation, and increased the proportion of cells in the G0-G1 phase of the cell cycle. This concurs with previous work showing HOXB4 to be a key, positive regulator of HSPC expansion (Antonchuk et al., 2002; Kyba et al., 2002). The longevity of the cultures confirms its effect on putative stem cells as well as more differentiated progenitor populations. The specificity of the inhibitory effect of the HOX hexapeptide on these gene targets is underlined by its reversibility, with gene transcription and cell growth resuming on HXP peptide removal. The protection of pluripotent HSPC in G0-G1 and its reversibility suggest a role for HXP peptide in maintaining and/or expanding haemopoietic stem/progenitor cells in vitro for prolonged periods. In addition, by temporarily stopping or slowing the cell cycle, HXP peptide could protect endogenous HSPC populations from the cytotoxic shock associated with many chemotherapeutic regimes.

In addition to blocking proliferation, HXP peptide also caused a rapid down-regulation of HOXB4 and HOXB8. The former is a known target of HOX genes, and is also subject to autoregulation, which may explain its sensitivity to HXP peptide. HOXB8 may also be regulated in this manner. The down-regulation of HOXB4 in HSPCs may account in part for the growth inhibitory effect of HXP peptide, especially as it is reversible over the same time course as the inhibition of cell growth by HXP peptide.

A number of other HOX/PBX targets have also been identified in this study. Most notable amongst these are the cell proliferation regulator N-RAS, and TERT, a component of the telomerase activity needed to maintain chromosomal stability. Both of these targets are down-regulated by HXP peptide. Target genes also include a diverse set of factors involved in the modulation of gene expression, including the DNA binding factor CTCF (Ohlsson et al., 2001) and the translation initiation factor EIF4E (Thornton et al., 2003).

In addition to HSPC regulation, HOX gene dysregulation has been implicated in some leukaemias (Owens and Hawley, 2002). AML is a heterogeneous leukaemia characterised by blockage of myeloid differentiation at different stages, which define distinct AML subtypes. We have shown, using myeloid leukaemic cell lines arrested at different stages of development, that the effect of HXP is not dependent on the developmental stage of the target cell. Thus it is likely to be therapeutically beneficial in both primary AML and mature myeloid leukaemias. In addition HXP peptide reduced the proportion of cells in phase G0-G1 of the cell cycle. This effect was apparent within two hours, and it was accompanied by specific changes in gene expression. In common with HSPCs, HXP peptide treatment of all four leukaemia lines resulted in the down-regulation of HOXB4 and HOXB8, and in the up-regulation of CD38, a marker of cellular differentiation. It is noteworthy that the majority of HOX/PBX target genes that were blocked by HXP peptide in the HSPC population are not affected in these leukaemia—derived cell lines. This implies that the regulation of these genes differs between cell types, and may be activated by different transcription factors in different contexts. The only exception to this was the oncogene N-RAS, which is strongly down-regulated in both HSPCs and in all four of the leukaemic cell lines. There may be a more complete dependence on HOX/PBX transcription factors in N-RAS regulation, and it is possible that N-RAS is the link between HOX gene over-expression and cellular transformation.

The properties of HXP peptide described here indicate that it could have a number of therapeutic uses. The results of this study also suggest a role for HOX/PBX interactions in acute myeloid and perhaps lymphoid leukaemias, in agreement with recent work showing that HOX genes are required for the transformation of cells by Murine Leukaemia Virus (Ayton and Cleary, 2003). Blocking these HOX/PBX interactions using HXP peptide may then be a means of preventing leukaemia cell growth in vivo. In addition, by increasing the proportion of cells entering the cell cycle, it could also increase their sensitivity to other chemotherapeutic reagents.

EXAMPLE 4

Methods

The methods used were the same as those described in the earlier Examples, unless otherwise specified.

1. Specific Conditions for Malignant Cell Line Culture.

Solid tumour cell lines (Cancer Research UK) were seeded at $4\times10^4$ cells/ml, in a liquid culture system made of appropriate medium (see table, Sigma-Aldrich, UK) supplemented with 10% FCS (Sigma Aldrich) and penstrep (1% Sigma). All cell lines were grown with HXP peptide (as in Example 3, 20 µg/ml or 200 µg/ml) or control peptide CXP (20 µg/ml or 200 µg/ml).

| Cell lines | Medium |
| --- | --- |
| JAR | DMEM |
| LNCAP | DMEM |
| HT1376 | DMEM + 1% non essential amino acid |
| HELA | RPMI |
| A375P | RPMI |
| DX3 | RPMI |
| MES | McCoy's 5A |
| SKBR3 | DMEM (1:1) HAM's F10 |
| NCI-h510A | RPMI |
| HTB47 | McCoy's 5A |
| PSN-1 | DMEM |
| PANC-TU1 | DMEM |

KG1a, KG1, HL60 and U937 cell lines (EACC, UK) were seeded at $5\times10^4$ cells/ml, in a liquid culture system made of RPMI-1640 medium (Life Technologies, UK) supplemented with 10% FCS (Sigma Aldrich) and gentamicin (50 µg/ml Life Technologies) in triplicates. All cell lines were grown with HXP peptide peptide (20 µg/ml) or control peptide (20 µg/ml).

Cell lines were cultured for various time points at 37° C., 5% CO2 in humidified atmosphere and enumerated at various time points.

2. Human HOX RT-PCR Sequences.

The sequences of RT-PCR primers used are set out below. For each primer pair, the amplified region is given in relation to the known gene sequence as available through GenBank (http://www.ncbi.nlm.nih.gov/entrez).

| Gene | GenBank reference | Forward and reverse primers |
|---|---|---|
| HOXA1 | U10421; 511-663 153 bp | F: 5' CTGGCCCTGGCTACGTATAA 3'<br>R: 5' TCCAACTTTCCCTGTTTTGG 3' |
| HOXB1 | NM_002144; 176 to 332; 157 bp | F: 5' TTCAGCAGAACTCCGGCTAT 3'<br>R: 5' CCTCCGTCTCCTTCTGATTG 3' |
| HOXD1 | NM_024501; 929 to 1160; 232 bp | F: 5' TTCAGCACCAAGCAACTGAC 3'<br>R: 5' TAGTGGGGGTTGTTCCAGAG 3' |
| HOXA2 | NM_006735; 1027 to 1202; 176 bp | F: 5' TTCAGCAAAATGCCCTCTCT 3'<br>R: 5' TAGGCCAGCTCCACAGTTCT 3' |
| HOXB2 | NM_002145; 9 to 267; 259 bp | F: 5' CTCCCAAAATCGCTCCATTA 3'<br>R: 5' GAAAGGAGGAGGAGGAGGAA 3' |
| HOXA3 | NM_030661; 1525 to 1751; 227 bp | F: 5' ACCTGTGATAGTGGGCTTGG 3'<br>R: 5' ATACAGCCATTCCAGCAACC 3' |
| HOXB3 | NM_002146; 1970 to 2268; 299 bp | F: 5' TATGGCCTCAACCACCTTTC 3'<br>R: 5' AAGCCTGGGTACCACCTTCT 3' |
| HOXD3 | NM_006898; 492 to 667; 176 bp | F: 5' CAGCCTCCTGGTCTGAACTC 3'<br>R: 5' ATCCAGGGGAAGATCTGCTT 3' |
| HOXA4 | NM_002141; 633 to 903; 271 bp | F: 5' CCCTGGATGAAGAAGATCCA 3'<br>R: 5' AATTGGAGGATCGCATCTTG 3' |
| HOXB4 | NM_024015; 593 to 747; 155 bp | F: 5' TCTTGGAGCTGGAGAAGGAA 3'<br>R: 5' GTTGGGCAACTTGTGGTCTT 3' |
| HOXC4 | NM_014620; 1121 to 1396; 276 bp | F: 5' CGCTCGAGGACAGCCTATAC 3'<br>R: 5' GCTCTGGGAGTGGTCTTCAG 3' |
| HOXD4 | NM_014621; 23 to 195; 173 bp | F: 5' TCAAATGTGCCATAGCAAGC 3'<br>R: 5' TCCATAGGGCCCTCCTACTT 3' |
| HOXA5 | NM_019102; 796 to 988; 193 bp | F: 5' CCGGAGAATGAAGTGGAAAA 3'<br>R: 5' ACGAGAACAGGGCTTCTTCA 3' |
| HOXB5 | NM_002147; 1543 to 1731; 189 bp | F: 5' AAGGCCTGGTCTGGGAGTAT 3'<br>R: 5' GCATCCACTCGCTCACTACA 3' |
| HOXC5 | NM_019953; 555 to 822; 268 bp | F: 5' CAGTTACACGCGCTACCAGA 3'<br>R: 5' AGAGAGGAAAGGCGAAAAGG 3' |
| HOXA6 | NM_024014; 361 to 518; 158 bp | F: 5' AAAGCACTCCATGACGAAGG 3'<br>R: 5' TCCTTCTCCAGCTCCAGTGT 3' |
| HOXB6 | NM_156037; 151 to 334; 184 bp | F: 5' ATTTCCTTCTGGCCCTCACT 3'<br>R: 5' GGAAGGTGGAGTTCACGAAA 3' |
| HOXC6 | NM_004503; 774 to 963; 190 bp | F: 5' AAGAGGAAAAGCGGGAAGAG 3'<br>R: 5' GGTCCACGTTTGACTCCCTA 3' |
| HOXA7 | NM_006896; 38 to 322; 285 bp | F: 5' TGGTGTAAATCTGGGGGTGT 3'<br>R: 5' TCTGATAAAGGGGGCTGTTG 3' |
| HOXB7 | NM_004502; 143 to 391; 249 bp | F: 5' CAGCCTCAAGTTCGGTTTTC 3'<br>R: 5' CGGAGAGGTTCTGCTCAAAG 3' |
| HOXB8 | NM_024016; 964 to 1228; 265 bp | F: 5' GTAGGCTTCAGCTGGGACTG 3'<br>R: 5' GGGAGCCTTTGCTTAAATCC 3' |
| HOXC8 | NM_022658; 390 to 539; 150 bp | F: 5' CTCAGGCTACCAGCAGAACC 3'<br>R: 5' TTGGCGGAGGATTTACAGTC 3' |
| HOXD8 | NM_019558; 1167 to 1456; 290 bp | F: 5' TCAAATGTTTCCGTGGATGA 3'<br>R: 5' GCTCTTGGGCTTCCTTTTTC 3' |
| HOXA9 | | F: 5' AATAACCCAGCAGCCAACTG 3'<br>R: 5' ATTTTCATCCTGCGGTTCTG 3' |
| HOXB9 | NM_024017; 533 to 730; 198 bp | F: 5' TAATCAAAGACCCGGCTACG 3'<br>R: 5' CTACGGTCCCTGGTGAGGTA 3' |

-continued

| Gene | GenBank reference | Forward and reverse primers |
|---|---|---|
| HOXC9 | NM_006897; 704 to 893; 190 bp | F: 5' AGACGCTGGAACTGGAGAAG 3'<br>R: 5' AGGCTGGGTAGGGTTTAGGA 3' |
| HOXD9 | NM_014213; 1803 to 2038; 236 bp | F: 5' TCCCCCATGTTTCTGAAAAG 3'<br>R: 5' GGGCTCCTCTAAGCCTCACT 3' |
| HOXA10 | NM_018951; 1040 to 1198; 159 bp | F: 5' ACACTGGAGCTGGAGAAGGA 3'<br>R: 5' GATCCGGTTTTCTCGATTCA 3' |
| HOXC10 | NM_017409; 982 to 1270; 289 bp | F: 5' CGCCTGGAGATTAGCAAGAC 3'<br>R: 5' GGTCCCTTGGAAGGAGAGTC 3' |
| HOXD10 | NM_002148; 364 to 517; 154 bp | F: 5' GCTCCTTCACCACCAACATT 3'<br>R: 5' AAATATCCAGGGACGGGAAC 3' |
| HOXA11 | NM_005523; 800 to 1078; 279 bp | F: 5' CGCTGCCCCTATACCAAGTA 3'<br>R: 5' GTCAAGGGCAAAATCTGCAT 3' |
| HOXC11 | NM_014212; 353 to 538; 186 bp | F: 5' CGGAACAGCTACTCCTCCTG 3'<br>R: 5' CAGGACGCTGTTCTTGTTGA 3' |
| HOXD11 | NM_021192; 302 to 554; 253 bp | F: 5' GGGGCTACGCTCCCTACTAC 3'<br>R: 5' GCTGCCTCGTAGAACTGGTC 3' |
| HOXC12 | NM_173860; 654 to 833; 180 bp | F: 5' CAAGCCCTATTCGAAGTTGC 3'<br>R: 5' GCTTGCTCCCTCAACAGAAG 3' |
| HOXD12 | NM_021193; 113 to 313; 201 bp | F: 5' CGCTTCCCCCTATCTCCTAC 3'<br>R: 5' CTTCGGGCGCATAGAACTTA 3' |
| HOXA13 | NM_000522; 1061 to 1236; 176 bp | F: 5' GGATATCAGCCACGACGAAT 3'<br>R: 5' ATTATCTGGGCAAAGCAACG 3' |
| HOXB13 | NM_006361; 154 to 387; 234 bp | F: 5' CTTGGATGGAGCCAAGGATA 3'<br>R: 5' CCGCCTCCAAAGTAACCATA 3' |
| HOXC13 | NM_017416; 1840 to 2009; 170 bp | F: 5' GTGGAAATCCAAGGAGGACA 3'<br>R: 5' TTGTTGAGGGACCCACTCTC 3' |
| HOXD13 | NM_000523; 868 to 1132; 265 bp | F: 5' GGGGATGTGGCTCTAAATCA 3'<br>R: 5' AACCTGGACCACATCAGGAG 3' |

Results

1. HXP Peptide Blocks the Proliferation of a Wide Range of Different Malignant Cell Lines.

Figure 11:
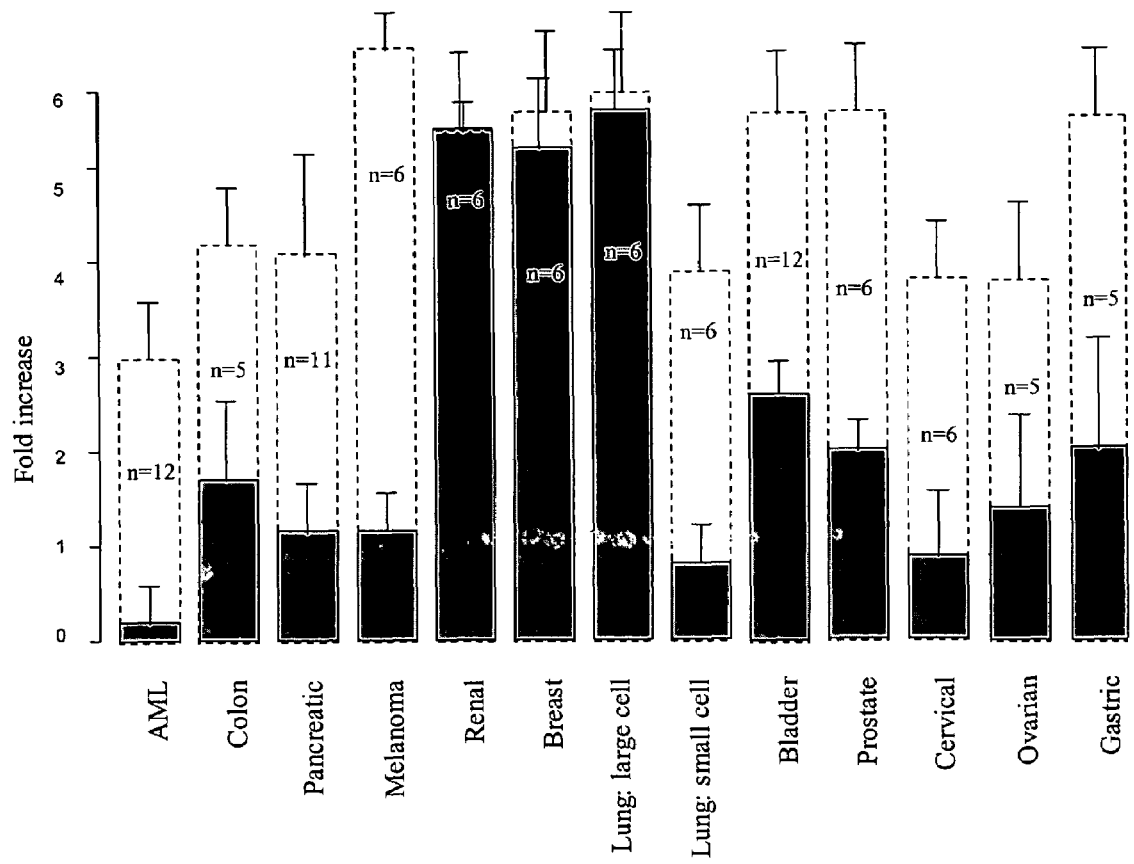
FIG. 11 shows that the HXP peptide blocks the proliferation of different malignant cell lines. A number of cell lines representing different malignancies were grown in culture for seven days, and HXP peptide or the control peptide CXP were added to a final concentration of 20 µg/ml on day 3. The bars represent the fold increase of each cell line over the seven days; the empty, dashed bars indicate the CXP peptide treated cells, whilst the solid bars indicate the addition of HXP peptide. Error bars represent the standard error the mean, and n is the number of experiments performed. The cell lines used were: AML—KG1a; Bladder—HT; Breast—SKBR3; Cervical—HeLa; Colon—Colo41; Gastric—MKN-45; Large cell lung cancer—MES; Melanoma—DX3; Ovarian—1847; Pancreatic—Panc-Tu1; Prostate—LNCAP; Renal—HT1376; Small cell lung cancer—NCI-h510A. The change in the expression of the HOX genes expressed by each cell line was assessed by RT-PCR on RNA extracted from the cells at the end of seven days. 'HOX gene inactivated' means that the level of expression of each of the listed HOX genes was at least five fold lower in the HXP peptide treated cells compared to the control. *Analysis not yet complete.

We tested the activity of HXP peptide on a number of different malignant cell lines using a similar assay to that described previously. A 20 μg/ml dose was sufficient to block the proliferation of cells derived from the following cancers: colorectal, pancreatic, small cell lung cancer, bladder cancer, prostate cancer, cervical, ovarian and gastric (FIG. 11), although no significant affect was observed with cells derived from renal, breast and non-small cell lung cancer. The reduction in proliferation was accompanied by specific changes in gene expression (FIG. 11), with the at least two different Hox genes being transcriptionaly silenced in each case. It is noteworthy that distinct sets of Hox genes are down-regulated in each cancer cell line, reflecting the importance of HXP peptide as a general inhibitor of HOX function and its consequentially broad affect on cancer cell proliferation.

2. Effect of HXP Peptide Concentration

Figure 12:
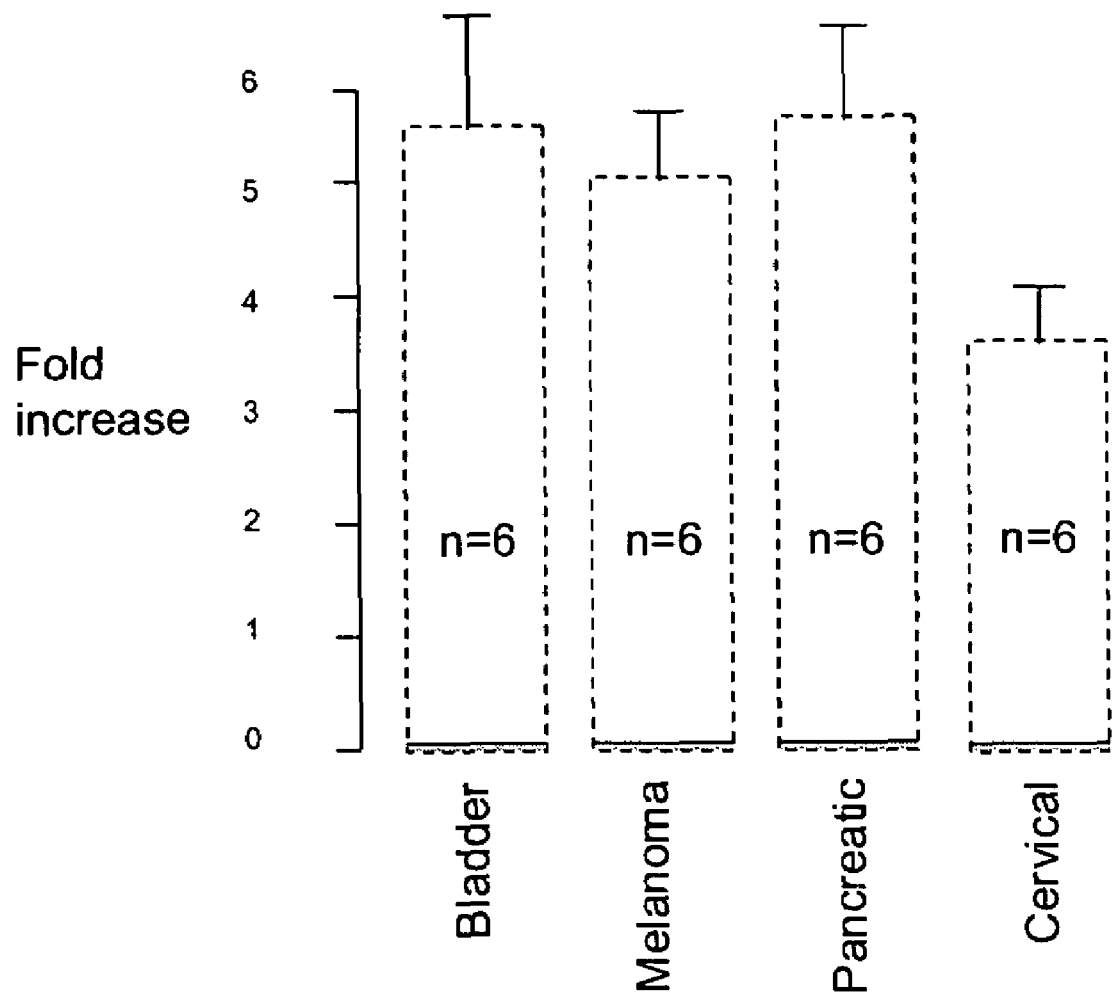
FIG. 12 shows that a higher dose of HXP peptide can ablate all cells in culture. A number of cell lines representing different malignancies were grown in culture for seven days, and HXP peptide or the control peptide CXP were added to a final concentration of 200 µg/ml on day 3. The bars represent the fold increase of each cell line over the seven days; the empty, dashed bars indicate the CXP peptide treated cells, whilst the solid bars indicate the addition of HXP peptide. Error bars represent the standard error the mean, and n is the number of experiments performed. The cell lines used were: Bladder—HT; Cervical—HeLa; Melenoma—DX3; Pancreatic—Panc-Tu1.

It is clear that use of the HXP peptide at 20 μg/ml causes a significant reduction in cell proliferation, and in some cases the fold increase is less than 1, i.e. the number of cells surviving after 7 days in culture is less than the starting population. It is possible therefore that an increased dose of HXP peptide could ablate all of the cells in the starting culture. This was tested using a dose of 200 mg/ml. This ten fold increase in dose caused the complete ablation of some malignancies (FIG. 12). The same concentration of control peptide had no significant affect on proliferation, indicating that the observed cell killing properties of HXP peptide are specific to this peptide, and not a result of non-specific toxicity.

3. Derivatives of HXP Peptide

Figure 13:
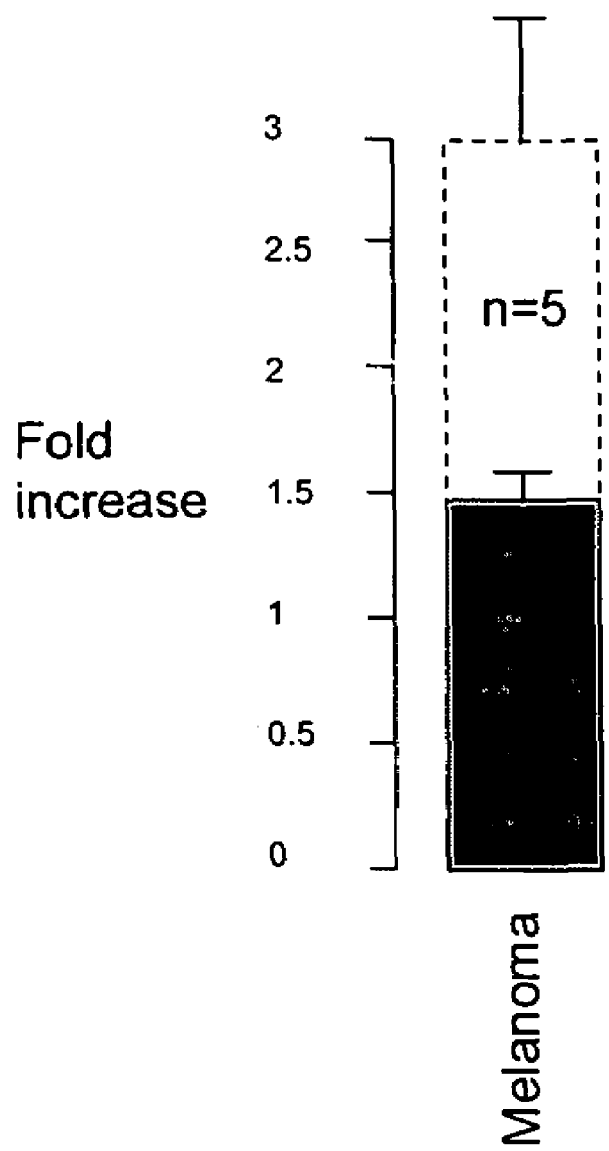
FIG. 13 shows that HXP4(10) blocks the proliferation of a melanoma (DX3) cell line. A number of cell lines representing different malignancies were grown in culture for seven days, and HXP4(10) or the control peptide CXP peptide were added to a final concentration of 20 μg/ml on day 3. The bars represent the fold increase over seven days; the empty, dashed bars indicate the CXP peptide treated cells, whilst the solid bars indicate the addition of HXP4(10). Error bars represent the standard error the mean, and n is the number of experiments performed.

We have examined whether a smaller peptide might be able to substitute for HXP peptide. One possibility is a peptide based only on the hexapeptide sequence, but with charge and hydrophobicity ratio that matches those required by previously characterised cell penetrating agents. This led to the design of a 10 amino acid peptide referred to as HXP4(10). This is a far smaller molecule that lacks the cell penetrating domain used by the original. HXP4(10) has the amino acid sequence WYPWMKKHHR (SEQ ID NO: 7). Like HXP peptide, HXP4(10) can also block the proliferation of some malignant cell lines in a highly specific manner (FIG. 13). It still shows significant activity against some malignant cell lines. The smaller size of HXP4(10) would significantly reduce production costs (by ca. 80%).

It was particularly noted that HXP4(10) was able to exert an effect on cell lines even though it does not include a specific cell penetration sequence. The presence of a cell penetration sequence in the peptides of the invention is not required for therapeutic utility. The ability of HXP4(10) to enter cells without the presence of a cell penetration sequence is a further, unexpected, advantage of the present invention.

4. Stability of HXP Peptide and HAP4(10)

Figure 14:
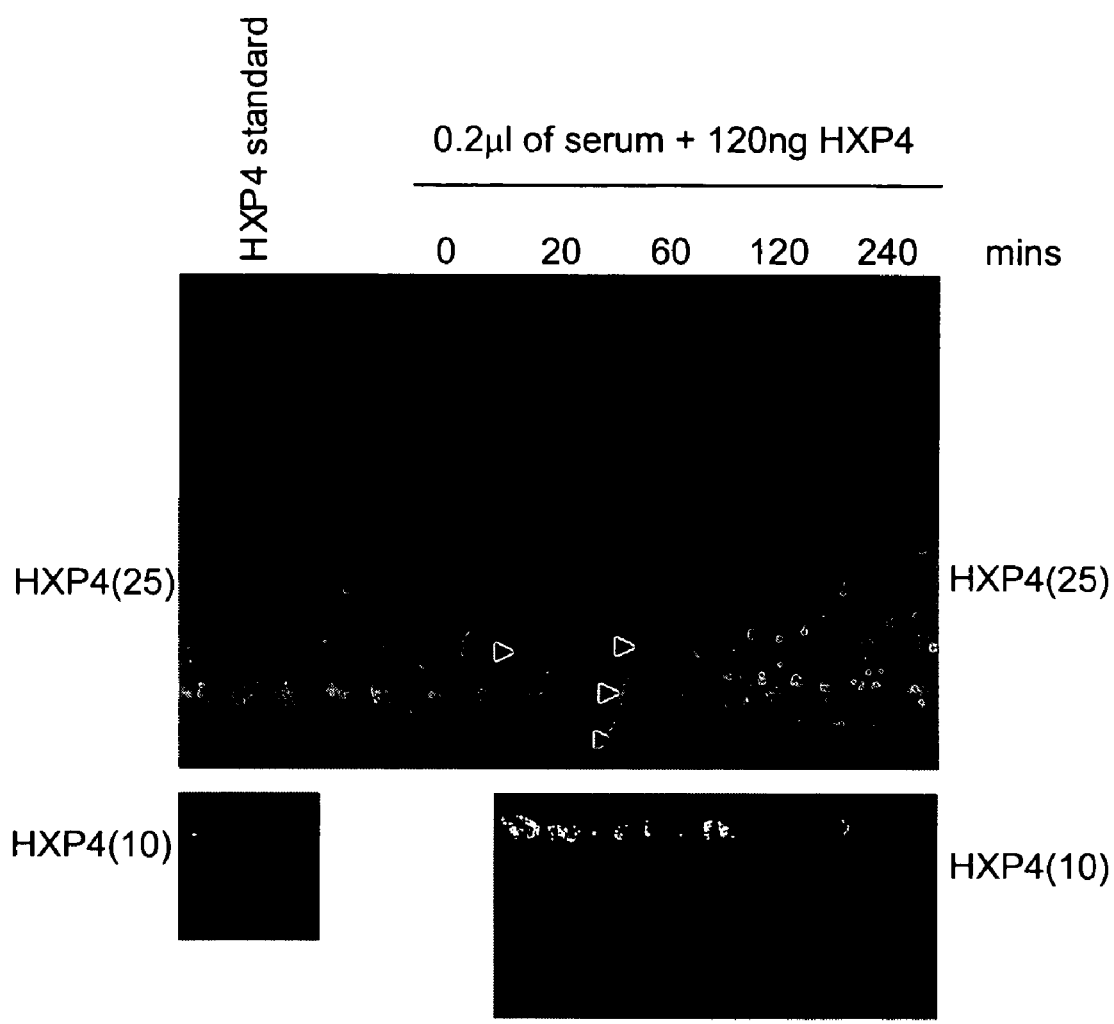
FIG. 14 shows the stability of HXP peptide in human serum. 30 μg of HXP(10) or HXP peptide were incubated in 50 μl of human serum at 37° C. for the times shown. Samples were run on a denaturing PAGE and silver stained. Arrow heads indicate likely HXP peptide degradation products.

The stability of HXP peptide and HXP4(10) have now been tested in human serum (FIG. 14). This gives an indication of how robust each would be when used in vivo. HXP peptide has a half life of one hour, and HXP4(10) has a half life of about 4 hours. This compares favourably with other peptide based pharmaceuticals; for example low molecular weight heparin, which is routinely used to prevent blood clotting, has a serum half life of only thirty minutes.

The invention claimed is:

1. A method of treating a disorder in which aberrant cell division occurs in a human or animal comprising administering to said human or animal a therapeutically effective amount of a peptide comprising the amino acid sequence:

$X_1 X_2 X_3 W M X_4 X_5 X_6 X_7$;

wherein $X_1$ is selected from W, T, PE, KQI, VV, PQT, H, RI and absent;

$X_2$ is Y;

$X_3$ is P;

$X_4$ is K or R;

$X_5$ is K, R or E;

$X_6$ is H, R, Q or K; and $X_7$ is H, S, R or K and wherein said disorder is a cancer.

2. The method according to claim 1 wherein said peptide $X_1$ to $X_7$ has the amino acid sequence W Y P W M K K H H R (SEQ ID NO: 7).

3. The method according to claim 1 wherein said peptide further comprises a cell penetration moiety.

4. The method according to claim 3 wherein said cell penetration moiety is linked directly to the carboxy-terminal of the peptide X1 to X7.

5. The method according to claim 3 or 4 wherein said cell penetration moiety has the amino acid sequence:

X8 Q I K I W F Q N R R M K W K K wherein X8 is R or Q.

6. The method according to claim 3 wherein said cell penetration moiety has the amino acid sequence

X8 Q X9 X10 X11 W F Q N X12 X13 M X14 W X15 X16 wherein

X8 is R or Q,

X9, X11 are each independently I or L, and

X10, X12, X13, X14, X15 and X16 are each independently K or R.

7. The method according to claim 3 wherein said cell penetration moiety has the amino acid sequence:

| | |
|---|---|
| QIRIWFQNRRMKWKK; | (SEQ ID NO: 10) |
| QIKIWFQNKRMKWKK; | (SEQ ID NO: 11) |
| QIKIWFQNKKMKWKK; | (SEQ ID NO: 12) |
| QIRIWFQNRKMKWKK; | (SEQ ID NO: 13) |

```
QIRIWFQNRRMRWKK;      (SEQ ID NO: 14)

QIRIWFQNRRMKWRK;      (SEQ ID NO: 15)

QIRIWFQNRRMKWKR;      (SEQ ID NO: 16)

QIRIWFQNRRMKWRR;      (SEQ ID NO: 17)

QIRIWFQNRRMKWKK;      (SEQ ID NO: 18)

QIKIWFQNRRMKWRK;      (SEQ ID NO: 19)

QIRIWFQNKRMKWRK;      (SEQ ID NO: 20)

QIKLWFQNRRMKWKK,      (SEQ ID NO: 21)

QLKLWFQNRRMKWKK;      (SEQ ID NO: 22) or

QLRIWFQNRRMKWKK;      (SEQ ID NO: 23).
```

8. The method according to claim 3 wherein said peptide has the sequence:

```
                                      (SEQ ID NO: 26)
W Y P W M K K H H R Q I K I W F Q N R R M K W K;
or (SEQ ID NO: 24)
W Y P W M K K H H R Q I K I W F Q N R R M K W K K.
```

9. The method according to claim 1 wherein said peptide has the sequence

```
          W Y P W M K K H H R (SEQ ID NO:7).
```

10. The method according to claim 1 wherein the increased cell division occurs in cells which express one or more Hox genes.

11. The method according to claim 1 wherein the increased cell division occurs in cells in which pre-B-cell transformation related gene (PBX) does not act as an oncogene.

12. A method according to claim 1 wherein said human or animal is also administered a cytotoxic or chemotherapeutic agent.

* * * * *

```
                        SEQUENCE LISTING

<160> NUMBER OF SEQ ID NOS: 119

<210> SEQ ID NO 1
<211> LENGTH: 11
<212> TYPE: PRT
<213> ORGANISM: Artificial Sequence
<220> FEATURE:
<223> OTHER INFORMATION: Peptide mimic of HOX Heptapeptide Region
<220> FEATURE:
<221> NAME/KEY: MISC_FEATURE
<222> LOCATION: (1)..(1)
<223> OTHER INFORMATION: Xaa may be present or absent, is a moiety
      attached via the available amino group or alternatively via the
      side chain of the adjacent amino acid residue, is preferably a
      peptide of 50 amino acids or less which is optionall substituted.
<220> FEATURE:
<221> NAME/KEY: MISC_FEATURE
<222> LOCATION: (2)..(2)
<223> OTHER INFORMATION: Xaa may be present or absent, is one or more
      amino acids, and is preferably W, T, PE, KQI, VV, PQT, H or RI.
<220> FEATURE:
<221> NAME/KEY: MISC_FEATURE
<222> LOCATION: (3)..(3)
<223> OTHER INFORMATION: Xaa is an amino acids with an aromatic side
      chain, preferably Y, F or W.
<220> FEATURE:
<221> NAME/KEY: MISC_FEATURE
<222> LOCATION: (4)..(4)
<223> OTHER INFORMATION: Xaa is the amino acid P or D.
<220> FEATURE:
<221> NAME/KEY: MISC_FEATURE
<222> LOCATION: (7)..(7)
<223> OTHER INFORMATION: Xaa is an amino acid with a basic side chain,
      preferably K, R or H.
<220> FEATURE:
<221> NAME/KEY: MISC_FEATURE
<222> LOCATION: (8)..(8)
<223> OTHER INFORMATION: Xaa is an amino acid with a charged side chain,
      preferably a basic side chain, especially preferably K, R, E, H,
      D, N or Q.
<220> FEATURE:
<221> NAME/KEY: MISC_FEATURE
<222> LOCATION: (9)..(9)
<223> OTHER INFORMATION: Xaa is an amino acid with a charged side chain,
      preferably a basic side chain, especially preferably K, R, E, H,
      D, N or Q.
<220> FEATURE:
<221> NAME/KEY: MISC_FEATURE
<222> LOCATION: (10)..(10)
<223> OTHER INFORMATION: Xaa is an amino acid with a basic side chain or
      serine, especially preferably H, S, R, or K or a functionally
      equivalent derivative, variant or fragment thereof.
<220> FEATURE:
<221> NAME/KEY: MISC_FEATURE
<222> LOCATION: (11)..(11)
<223> OTHER INFORMATION: Xaa may be present or absent, is a moiety
      attached via the available carboyxl group or alternatively via the
      side chain of the adjacent amino acid residue, is preferably a
      peptide of 50 amino acids or less which is optionall substituted.

<400> SEQUENCE: 1

Xaa Xaa Xaa Xaa Trp Met Xaa Xaa Xaa Xaa Xaa
1               5                   10

<210> SEQ ID NO 2
```

```
<211> LENGTH: 9
<212> TYPE: PRT
<213> ORGANISM: Artificial Sequence
<220> FEATURE:
<223> OTHER INFORMATION: Peptide mimic of HOX heptapeptide region
<220> FEATURE:
<221> NAME/KEY: MISC_FEATURE
<222> LOCATION: (1)..(1)
<223> OTHER INFORMATION: Xaa may be present or absent, is one or more
      amino acids, and is preferably  W, T, PE, KQI, VV, PQT, H or RI.
<220> FEATURE:
<221> NAME/KEY: MISC_FEATURE
<222> LOCATION: (2)..(2)
<223> OTHER INFORMATION: Xaa is an amino acid with an aromatic side
      chain, preferably Y, F or W.
<220> FEATURE:
<221> NAME/KEY: MISC_FEATURE
<222> LOCATION: (3)..(3)
<223> OTHER INFORMATION: Xaa is the amino acid P or D
<220> FEATURE:
<221> NAME/KEY: MISC_FEATURE
<222> LOCATION: (6)..(6)
<223> OTHER INFORMATION: Xaa is an amino acid with a basic side chain,
      preferably K, R or H.
<220> FEATURE:
<221> NAME/KEY: MISC_FEATURE
<222> LOCATION: (7)..(7)
<223> OTHER INFORMATION: Xaa is an amino acid with a charged side chain,
      preferably a basic side chain, especially preferably K, R, E, H,
      D, N, or Q.
<220> FEATURE:
<221> NAME/KEY: MISC_FEATURE
<222> LOCATION: (8)..(8)
<223> OTHER INFORMATION: Xaa is an amino acid with a charged side chain,
      preferably a basic side chain, especially preferably K, R, E, H,
      D, N, or Q.
<220> FEATURE:
<221> NAME/KEY: MISC_FEATURE
<222> LOCATION: (9)..(9)
<223> OTHER INFORMATION: Xaa is an amino acid with a basic side chain or
      serine, especially preferably H, S, R or K.

<400> SEQUENCE: 2

Xaa Xaa Xaa Trp Met Xaa Xaa Xaa Xaa
1               5

<210> SEQ ID NO 3
<211> LENGTH: 11
<212> TYPE: PRT
<213> ORGANISM: Artificial Sequence
<220> FEATURE:
<223> OTHER INFORMATION: Peptide mimic of HOX heptapeptide region.
<220> FEATURE:
<221> NAME/KEY: MISC_FEATURE
<222> LOCATION: (1)..(1)
<223> OTHER INFORMATION: Xaa may be present or absent, is a moiety
      attached via the available amino group or alternatively via the
      side chain of the adjacent amino acid residue, is preferably a
      peptide of 50 amino acids or less which is optionally substitute
<220> FEATURE:
<221> NAME/KEY: MISC_FEATURE
<222> LOCATION: (2)..(2)
<223> OTHER INFORMATION: Xaa may be present or absent, is one or more
      amino acids, and is preferably W, T, PE, KQI, VV, PQT, H or RI.
<220> FEATURE:
<221> NAME/KEY: MISC_FEATURE
<222> LOCATION: (3)..(3)
<223> OTHER INFORMATION: Xaa is the amino acid Y or F.
<220> FEATURE:
<221> NAME/KEY: MISC_FEATURE
<222> LOCATION: (4)..(4)
<223> OTHER INFORMATION: Xaa is the amino acid P or D.
<220> FEATURE:
<221> NAME/KEY: MISC_FEATURE
<222> LOCATION: (7)..(7)
<223> OTHER INFORMATION: Xaa is the amino acid K or R
<220> FEATURE:
```

```
<221> NAME/KEY: MISC_FEATURE
<222> LOCATION: (8)..(8)
<223> OTHER INFORMATION: Xaa is the amino acid K, R or E.
<220> FEATURE:
<221> NAME/KEY: MISC_FEATURE
<222> LOCATION: (9)..(9)
<223> OTHER INFORMATION: Xaa is the amino acid H, R, Q or K.
<220> FEATURE:
<221> NAME/KEY: MISC_FEATURE
<222> LOCATION: (10)..(10)
<223> OTHER INFORMATION: Xaa is the amino acid H, S, R or K.
<220> FEATURE:
<221> NAME/KEY: MISC_FEATURE
<222> LOCATION: (11)..(11)
<223> OTHER INFORMATION: Xaa may be present or absent, is a moiety
      attached via the available carboyxl group or alternatively via the
      side chain of the adjacent amino acid residue, is preferably a
      peptide of 50 amino acids or less which is optionally substit

<400> SEQUENCE: 3

Xaa Xaa Xaa Xaa Trp Met Xaa Xaa Xaa Xaa Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Peptide mimic of HOX heptapeptide region
<220> FEATURE:
<221> NAME/KEY: MISC_FEATURE
<222> LOCATION: (1)..(1)
<223> OTHER INFORMATION: Xaa may be present or absent, is a moiety
      attached via the available amino group or alternatively via the
      side chain of the adjacent amino acid residue, is preferably a
      peptide of 50 amino acids or less which is optionally substitute
<220> FEATURE:
<221> NAME/KEY: MISC_FEATURE
<222> LOCATION: (2)..(2)
<223> OTHER INFORMATION: Xaa may be present or absent, is one or more
      amino acids, and is preferably W, T, PE, KQI, VV, PQT, H or RI.
<220> FEATURE:
<221> NAME/KEY: MISC_FEATURE
<222> LOCATION: (7)..(7)
<223> OTHER INFORMATION: Xaa is the amino acid K or R.
<220> FEATURE:
<221> NAME/KEY: MISC_FEATURE
<222> LOCATION: (8)..(8)
<223> OTHER INFORMATION: Xaa is the amino acid K, R or E.
<220> FEATURE:
<221> NAME/KEY: MISC_FEATURE
<222> LOCATION: (9)..(9)
<223> OTHER INFORMATION: Xaa is the amino acid H, R, Q or K.
<220> FEATURE:
<221> NAME/KEY: MISC_FEATURE
<222> LOCATION: (10)..(10)
<223> OTHER INFORMATION: Xaa is the amino acid H, S, R or K.
<220> FEATURE:
<221> NAME/KEY: MISC_FEATURE
<222> LOCATION: (11)..(11)
<223> OTHER INFORMATION: Xaa may be present or absent, is a moiety
      attached via the available carboyxl group or alternatively via the
      side chain of the adjacent amino acid residue, is preferably a
      peptide of 50 amino acids or less which is optionally substituted.

<400> SEQUENCE: 4

Xaa Xaa Tyr Pro Trp Met Xaa Xaa Xaa Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Peptide mimic of HOX heptapeptide region
```

```
<220> FEATURE:
<221> NAME/KEY: MISC_FEATURE
<222> LOCATION: (1)..(1)
<223> OTHER INFORMATION: Xaa may be present or absent, is a moiety
      attached via the available amino group or alternatively via the
      side chain of the adjacent amino acid residue, is preferably a
      peptide of 50 amino acids or less which is optionally substitute
<220> FEATURE:
<221> NAME/KEY: MISC_FEATURE
<222> LOCATION: (11)..(11)
<223> OTHER INFORMATION: Xaa may be present or absent, is a moiety
      attached via the available carboyxl group or alternatively via the
      side chain of the adjacent amino acid residue, is preferably a
      peptide of 50 amino acids or less which is optionally substit

<400> SEQUENCE: 5

Xaa Trp Tyr Pro Trp Met Lys Lys His His Xaa
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Peptide mimic of HOX heptapeptide region

<400> SEQUENCE: 6

Trp Tyr Pro Trp Met Lys Lys His His
1               5

<210> SEQ ID NO 7
<211> LENGTH: 10
<212> TYPE: PRT
<213> ORGANISM: Artificial Sequence
<220> FEATURE:
<223> OTHER INFORMATION: Peptide mimic of HOX heptapeptide region

<400> SEQUENCE: 7

Trp Tyr Pro Trp Met Lys Lys His His Arg
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Peptide cell penetration moiety
<220> FEATURE:
<221> NAME/KEY: MISC_FEATURE
<222> LOCATION: (1)..(1)
<223> OTHER INFORMATION: Xaa is the amino acid R or Q or functionally
      equivalent derivative, variant or fragment thereof.

<400> SEQUENCE: 8

Xaa Gln Ile Lys Ile Trp Phe Gln Asn Arg Arg Met Lys Trp Lys Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Peptide cell penetration moiety
<220> FEATURE:
<221> NAME/KEY: MISC_FEATURE
<222> LOCATION: (1)..(1)
<223> OTHER INFORMATION: Xaa is the amino acid R or Q or absent.
<220> FEATURE:
<221> NAME/KEY: MISC_FEATURE
<222> LOCATION: (3)..(3)
<223> OTHER INFORMATION: Xaa is the amino acid I or L.
```

```
<220> FEATURE:
<221> NAME/KEY: MISC_FEATURE
<222> LOCATION: (4)..(4)
<223> OTHER INFORMATION: Xaa is the amino acid K or R.
<220> FEATURE:
<221> NAME/KEY: MISC_FEATURE
<222> LOCATION: (5)..(5)
<223> OTHER INFORMATION: Xaa is the amino acid I or L.
<220> FEATURE:
<221> NAME/KEY: MISC_FEATURE
<222> LOCATION: (10)..(10)
<223> OTHER INFORMATION: Xaa is the amino acid K or R.
<220> FEATURE:
<221> NAME/KEY: MISC_FEATURE
<222> LOCATION: (11)..(11)
<223> OTHER INFORMATION: Xaa is the amino acid K or R
<220> FEATURE:
<221> NAME/KEY: MISC_FEATURE
<222> LOCATION: (13)..(13)
<223> OTHER INFORMATION: Xaa is the amino acid K or R.
<220> FEATURE:
<221> NAME/KEY: MISC_FEATURE
<222> LOCATION: (15)..(15)
<223> OTHER INFORMATION: Xaa is the amino acid K or R.
<220> FEATURE:
<221> NAME/KEY: MISC_FEATURE
<222> LOCATION: (16)..(16)
<223> OTHER INFORMATION: Xaa is the amino acid K or R.

<400> SEQUENCE: 9

Xaa Gln Xaa Xaa Xaa Trp Phe Gln Asn Xaa Xaa Met Xaa Trp Xaa Xaa
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 10

Gln Ile Arg Ile Trp Phe Gln Asn Arg Arg Met Lys Trp Lys Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 11

Gln Ile Lys Ile Trp Phe Gln Asn Lys Arg Met Lys Trp Lys Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 12

Gln Ile Lys Ile Trp Phe Gln Asn Lys Lys Met Lys Trp Lys Lys
1               5                   10                  15

<210> SEQ ID NO 13
<211> LENGTH: 15
<212> TYPE: PRT
<213> ORGANISM: Artificial Sequence
<220> FEATURE:
```

<223> OTHER INFORMATION: Peptide cell penetration moiety

<400> SEQUENCE: 13

Gln Ile Arg Ile Trp Phe Gln Asn Arg Lys Met Lys Trp Lys Lys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 14

Gln Ile Arg Ile Trp Phe Gln Asn Arg Arg Met Arg Trp Lys Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 15

Gln Ile Arg Ile Trp Phe Gln Asn Arg Arg Met Lys Trp Arg Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 16

Gln Ile Arg Ile Trp Phe Gln Asn Arg Arg Met Lys Trp Lys Arg
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 17

Gln Ile Arg Ile Trp Phe Gln Asn Arg Arg Met Lys Trp Arg Arg
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 18

Gln Ile Arg Ile Trp Phe Gln Asn Arg Arg Met Lys Trp Lys Lys
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Peptide cell penetration moiety

```
<400> SEQUENCE: 19

Gln Ile Lys Ile Trp Phe Gln Asn Arg Arg Met Lys Trp Arg Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 20

Gln Ile Arg Ile Trp Phe Gln Asn Lys Arg Met Lys Trp Arg Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Peptide cell penetration moiety

<400> SEQUENCE: 21

Gln Ile Lys Leu Trp Phe Gln Asn Arg Arg Met Lys Trp Lys Lys
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Peptide cell penetration moiety

<400> SEQUENCE: 22

Gln Leu Lys Leu Trp Phe Gln Asn Arg Arg Met Lys Trp Lys Lys
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Peptide cell penetration moiety

<400> SEQUENCE: 23

Gln Leu Arg Ile Trp Phe Gln Asn Arg Arg Met Lys Trp Lys Lys
1               5                   10                  15

<210> SEQ ID NO 24
<211> LENGTH: 25
<212> TYPE: PRT
<213> ORGANISM: Artificial sequence
<220> FEATURE:
<223> OTHER INFORMATION: Peptide comprising mimic of HOX heptapeptide
      region and cell penetration moiety

<400> SEQUENCE: 24

Trp Tyr Pro Trp Met Lys Lys His His Arg Gln Ile Lys Ile Trp Phe
1               5                   10                  15

Gln Asn Arg Arg Met Lys Trp Lys Lys
            20                  25

<210> SEQ ID NO 25
<211> LENGTH: 25
<212> TYPE: PRT
```

```
<213> ORGANISM: Artificial sequence
<220> FEATURE:
<223> OTHER INFORMATION: Control Peptide

<400> SEQUENCE: 25

Trp Ala Pro Trp Glu Asp Asp His His Arg Gln Ile Lys Ile Trp Phe
1               5                   10                  15

Gln Asn Arg Arg Met Lys Trp Lys Lys
            20                  25

<210> SEQ ID NO 26
<211> LENGTH: 24
<212> TYPE: PRT
<213> ORGANISM: Artificial sequence
<220> FEATURE:
<223> OTHER INFORMATION: Peptide comprising mimic of HOX heptapetide
      region and cell penetration moiety

<400> SEQUENCE: 26

Trp Tyr Pro Trp Met Lys Lys His His Arg Gln Ile Lys Ile Trp Phe
1               5                   10                  15

Gln Asn Arg Arg Met Lys Trp Lys
            20

<210> SEQ ID NO 27
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 27
cagtctgacc agcgtgaaaa                                           20

<210> SEQ ID NO 28
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 28
ggccatccaa atctgtccta                                           20

<210> SEQ ID NO 29
<211> LENGTH: 21
<212> TYPE: DNA
<213> ORGANISM: Artificial sequence
<220> FEATURE:
<223> OTHER INFORMATION: Primer for RT-PCR.

<400> SEQUENCE: 29
atgtaccctg gcattgccga c                                         21

<210> SEQ ID NO 30
<211> LENGTH: 21
<212> TYPE: DNA
<213> ORGANISM: Artificial sequence
<220> FEATURE:
<223> OTHER INFORMATION: Primer for RT-PCR.

<400> SEQUENCE: 30
gactcgtcat actcctgctt g                                         21

<210> SEQ ID NO 31
```

-continued

```
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 31
tgaagcctag cctgtcacct                                               20

<210> SEQ ID NO 32
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 32
cgcacagctg gaggtcttat                                               20

<210> SEQ ID NO 33
<211> LENGTH: 21
<212> TYPE: DNA
<213> ORGANISM: Artificial sequence
<220> FEATURE:
<223> OTHER INFORMATION: Primer for RT-PCR.

<400> SEQUENCE: 33
gggtgataca tggtggaaga g                                             21

<210> SEQ ID NO 34
<211> LENGTH: 21
<212> TYPE: DNA
<213> ORGANISM: Artificial sequence
<220> FEATURE:
<223> OTHER INFORMATION: Primer for RT-PCR.

<400> SEQUENCE: 34
tgtgcaagat gaatcctcag g                                             21

<210> SEQ ID NO 35
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 35
aataacccag cagccaactg                                               20

<210> SEQ ID NO 36
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 36
attttcatcc tgcggttctg                                               20

<210> SEQ ID NO 37
<211> LENGTH: 21
<212> TYPE: DNA
<213> ORGANISM: Artificial sequence
<220> FEATURE:
<223> OTHER INFORMATION: Primer for RT-PCR.

<400> SEQUENCE: 37
```

```
agcgattacc tacccagcga c                                              21

<210> SEQ ID NO 38
<211> LENGTH: 18
<212> TYPE: DNA
<213> ORGANISM: Artificial sequence
<220> FEATURE:
<223> OTHER INFORMATION: Primer for RT-PCR.

<400> SEQUENCE: 38
agggtcccgg caggccgc                                                  18

<210> SEQ ID NO 39
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 39
tggagctgga gaaggagttc                                                20

<210> SEQ ID NO 40
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 40
cgctccagct tctgtttctc                                                20

<210> SEQ ID NO 41
<211> LENGTH: 25
<212> TYPE: PRT
<213> ORGANISM: Artificial sequence
<220> FEATURE:
<223> OTHER INFORMATION: Control Peptide

<400> SEQUENCE: 41

Trp Cys Cys Leu Ala Asp Arg His Gly Arg Gln Ile Lys Ile Trp Phe
1               5                   10                  15

Gln Asn Arg Arg Met Lys Trp Lys Lys
            20                  25

<210> SEQ ID NO 42
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 42
ctggccctgg ctacgtataa                                                20

<210> SEQ ID NO 43
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 43
tccaactttc cctgttttgg                                                20
```

<210> SEQ ID NO 44
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 44
ttcagcagaa ctccggctat                    20

<210> SEQ ID NO 45
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 45
cctccgtctc cttctgattg                    20

<210> SEQ ID NO 46
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 46
ttcagcacca agcaactgac                    20

<210> SEQ ID NO 47
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 47
tagtgggggt tgttccagag                    20

<210> SEQ ID NO 48
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 48
ttcagcaaaa tgccctctct                    20

<210> SEQ ID NO 49
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 49
taggccagct ccacagttct                    20

<210> SEQ ID NO 50
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 50
ctcccaaaat cgctccatta                                          20

<210> SEQ ID NO 51
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 51
gaaaggagga ggaggaggaa                                          20

<210> SEQ ID NO 52
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 52
acctgtgata gtgggcttgg                                          20

<210> SEQ ID NO 53
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 53
atacagccat tccagcaacc                                          20

<210> SEQ ID NO 54
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 54
tatggcctca accacctttc                                          20

<210> SEQ ID NO 55
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 55
aagcctgggt accaccttct                                          20

<210> SEQ ID NO 56
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 56
cagcctcctg gtctgaactc                                          20

<210> SEQ ID NO 57

<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 57
atccagggga agatctgctt                                               20

<210> SEQ ID NO 58
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 58
ccctggatga agaagatcca                                               20

<210> SEQ ID NO 59
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 59
aattggagga tcgcatcttg                                               20

<210> SEQ ID NO 60
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 60
tcttggagct ggagaaggaa                                               20

<210> SEQ ID NO 61
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 61
gttgggcaac ttgtggtctt                                               20

<210> SEQ ID NO 62
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 62
cgctcgagga cagcctatac                                               20

<210> SEQ ID NO 63
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 63

```
gctctgggag tggtcttcag                                              20

<210> SEQ ID NO 64
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 64
tcaaatgtgc catagcaagc                                              20

<210> SEQ ID NO 65
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 65
tccatagggc cctcctactt                                              20

<210> SEQ ID NO 66
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 66
ccggagaatg aagtggaaaa                                              20

<210> SEQ ID NO 67
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 67
acgagaacag ggcttcttca                                              20

<210> SEQ ID NO 68
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 68
aaggcctggt ctgggagtat                                              20

<210> SEQ ID NO 69
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 69
gcatccactc gctcactaca                                              20

<210> SEQ ID NO 70
<211> LENGTH: 20
<212> TYPE: DNA
```

```
<213> ORGANISM: Artificial sequence
<220> FEATURE:
<223> OTHER INFORMATION: Primer for RT-PCR.

<400> SEQUENCE: 70
cagttacacg cgctaccaga                                               20

<210> SEQ ID NO 71
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 71
agagaggaaa ggcgaaaagg                                               20

<210> SEQ ID NO 72
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 72
aaagcactcc atgacgaagg                                               20

<210> SEQ ID NO 73
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 73
tccttctcca gctccagtgt                                               20

<210> SEQ ID NO 74
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 74
atttccttct ggccctcact                                               20

<210> SEQ ID NO 75
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 75
ggaaggtgga gttcacgaaa                                               20

<210> SEQ ID NO 76
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 76
aagaggaaaa gcgggaagag                                               20
```

<210> SEQ ID NO 77
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 77
ggtccacgtt tgactcccta                                               20

<210> SEQ ID NO 78
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 78
tggtgtaaat ctgggggtgt                                               20

<210> SEQ ID NO 79
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 79
tctgataaag ggggctgttg                                               20

<210> SEQ ID NO 80
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 80
cagcctcaag ttcggttttc                                               20

<210> SEQ ID NO 81
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 81
cggagaggtt ctgctcaaag                                               20

<210> SEQ ID NO 82
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 82
gtaggcttca gctgggactg                                               20

<210> SEQ ID NO 83
<211> LENGTH: 20
<212> TYPE: DNA
<213> ORGANISM: Artificial sequence
<220> FEATURE:

-continued

<223> OTHER INFORMATION: Primer for RT-PCR.

<400> SEQUENCE: 83
gggagccttt gcttaaatcc                                               20

<210> SEQ ID NO 84
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 84
ctcaggctac cagcagaacc                                               20

<210> SEQ ID NO 85
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 85
ttggcggagg atttacagtc                                               20

<210> SEQ ID NO 86
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 86
tcaaatgttt ccgtggatga                                               20

<210> SEQ ID NO 87
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 87
gctcttgggc ttccttttc                                                20

<210> SEQ ID NO 88
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 88
aataacccag cagccaactg                                               20

<210> SEQ ID NO 89
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 89
attttcatcc tgcggttctg                                               20

```
<210> SEQ ID NO 90
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 90
taatcaaaga cccggctacg                                               20

<210> SEQ ID NO 91
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 91
ctacggtccc tggtgaggta                                               20

<210> SEQ ID NO 92
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 92
agacgctgga actggagaag                                               20

<210> SEQ ID NO 93
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 93
aggctgggta gggtttagga                                               20

<210> SEQ ID NO 94
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 94
tcccccatgt ttctgaaaag                                               20

<210> SEQ ID NO 95
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 95
gggctcctct aagcctcact                                               20

<210> SEQ ID NO 96
<211> LENGTH: 20
<212> TYPE: DNA
<213> ORGANISM: Artificial sequence
<220> FEATURE:
<223> OTHER INFORMATION: Primer for RT-PCR.
```

```
<400> SEQUENCE: 96
acactggagc tggagaagga                                              20

<210> SEQ ID NO 97
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 97
gatccggttt tctcgattca                                              20

<210> SEQ ID NO 98
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 98
cgcctggaga ttagcaagac                                              20

<210> SEQ ID NO 99
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 99
ggtcccttgg aaggagagtc                                              20

<210> SEQ ID NO 100
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 100
gctccttcac caccaacatt                                              20

<210> SEQ ID NO 101
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 101
aaatatccag ggacgggaac                                              20

<210> SEQ ID NO 102
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 102
cgctgcccct ataccaagta                                              20

<210> SEQ ID NO 103
<211> LENGTH: 20
```

<212> TYPE: DNA
<213> ORGANISM: Artificial sequence
<220> FEATURE:
<223> OTHER INFORMATION: Primer for RT-PCR.

<400> SEQUENCE: 103
gtcaagggca aaatctgcat                                          20

<210> SEQ ID NO 104
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 104
cggaacagct actcctcctg                                          20

<210> SEQ ID NO 105
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 105
caggacgctg ttcttgttga                                          20

<210> SEQ ID NO 106
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 106
ggggctacgc tccctactac                                          20

<210> SEQ ID NO 107
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 107
gctgcctcgt agaactggtc                                          20

<210> SEQ ID NO 108
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 108
caagccctat tcgaagttgc                                          20

<210> SEQ ID NO 109
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 109
gcttgctccc tcaacagaag                    20

<210> SEQ ID NO 110
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 110 cgcttcccccc tatctcctac                   20

<210> SEQ ID NO 111
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 111
cttcgggcgc atagaactta                    20

<210> SEQ ID NO 112
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 112
ggatatcagc cacgacgaat                    20

<210> SEQ ID NO 113
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 113
attatctggg caaagcaacg                    20

<210> SEQ ID NO 114
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 114
cttggatgga gccaaggata                    20

<210> SEQ ID NO 115
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 115
ccgcctccaa agtaaccata                    20

<210> SEQ ID NO 116
<211> LENGTH: 20
<212> TYPE: DNA
<213> ORGANISM: Artificial sequence -continued

```
<220> FEATURE:
<223> OTHER INFORMATION: Primer for RT-PCR.

<400> SEQUENCE: 116
gtggaaatcc aaggaggaca                                              20

<210> SEQ ID NO 117
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 117
ttgttgaggg acccactctc                                              20

<210> SEQ ID NO 118
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 118
ggggatgtgg ctctaaatca                                              20

<210> SEQ ID NO 119
<211> LENGTH: 20
<212> TYPE: DNA
<213> ORGANISM: Artificial sequence
<220> FEATURE:
<223> OTHER INFORMATION: Primer for RT-PCR.

<400> SEQUENCE: 119
aacctggacc acatcaggag                                              20
```